(12) United States Patent
Sugiura et al.

(10) Patent No.: US 9,380,934 B2
(45) Date of Patent: Jul. 5, 2016

(54) OPTOMETRY APPARATUS CONTROLLER, OPTOMETRY SYSTEM, AND STORAGE MEDIUM HAVING OPTOMETRY APPARATUS PROGRAM STORED THEREIN

(71) Applicant: NIDEK CO., LTD., Aichi (JP)

(72) Inventors: Tomoyuki Sugiura, Aichi (JP); Yuichiro Kanazawa, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/412,673

(22) PCT Filed: Jul. 1, 2013

(86) PCT No.: PCT/JP2013/068047
§ 371 (c)(1),
(2) Date: Jan. 4, 2015

(87) PCT Pub. No.: WO2014/007216
PCT Pub. Date: Jan. 9, 2014

(65) Prior Publication Data
US 2015/0190047 A1    Jul. 9, 2015

(30) Foreign Application Priority Data

Jul. 4, 2012  (JP) ................................. 2012-150168
Jul. 11, 2012  (JP) ................................. 2012-155631

(51) Int. Cl.
| | | |
|---|---|---|
| A61B 3/02 | (2006.01) | |
| A61B 3/028 | (2006.01) | |
| A61B 3/036 | (2006.01) | |
| A61B 3/00 | (2006.01) | |
| G06F 19/00 | (2011.01) | |

(52) U.S. Cl.
CPC ............. *A61B 3/0285* (2013.01); *A61B 3/0033* (2013.01); *A61B 3/0058* (2013.01); *A61B 3/036* (2013.01); *G06F 19/3406* (2013.01)

(58) Field of Classification Search
CPC .......... A61B 3/04; A61B 3/02; A61B 3/0285; A61B 3/1015; A61B 3/103
USPC .................. 351/222, 223, 233, 234, 235, 246
See application file for complete search history.

(56) References Cited

U.S. PATENT DOCUMENTS

| | | |
|---|---|---|
| 6,619,799 B1 | 9/2003 | Dustin et al. |
| 2004/0032567 A1 | 2/2004 | Noda |

(Continued)

FOREIGN PATENT DOCUMENTS

| | | |
|---|---|---|
| JP | 2004229870 A2 | 8/2004 |
| JP | 2004329345 A2 | 11/2004 |

(Continued)

OTHER PUBLICATIONS

International Search Report dated Jul. 30, 2013 filed in PCT/JP2013/068047.

(Continued)

*Primary Examiner* — James Greece
(74) *Attorney, Agent, or Firm* — Rankin, Hill & Clark LLP

(57) ABSTRACT

In an optometry apparatus controller provided in an electric optometry apparatus including an optical element disposed in front of an examinee's eye and a switch mechanism that electrically switches the optical element, for instructing the switching of the optical element, the controller includes a touchscreen configured to display an operation screen for operating the electric optometry apparatus main body, displays, as the operation screen, a graphic image of a manual optometry apparatus as viewed from an operator side, the manual optometry apparatus including a plurality of operating units and being configured to switch the optical element disposed in front of the eye by an operation with respect to the operating units, and outputs a control signal to the electric optometry apparatus main body based on a touch input with respect to the graphic image on the touchscreen.

24 Claims, 24 Drawing Sheets

(56) References Cited

U.S. PATENT DOCUMENTS

| | | |
|---|---|---|
| 2004/0032568 A1 | 2/2004 | Noda |
| 2004/0218143 A1 | 11/2004 | Terabe |
| 2005/0080515 A1 | 4/2005 | Oumi |
| 2010/0033678 A1* | 2/2010 | Foster ............................ 351/223 |
| 2010/0157249 A1 | 6/2010 | Hosoi |
| 2011/0075099 A1 | 3/2011 | Kanazawa |
| 2011/0082704 A1* | 4/2011 | Blum ................................ 705/2 |

FOREIGN PATENT DOCUMENTS

| | | |
|---|---|---|
| JP | 2005111618 A2 | 4/2005 |
| JP | 2007068574 A2 | 3/2007 |
| JP | 2009005903 A2 | 1/2009 |
| JP | 2009061128 A2 | 3/2009 |
| JP | 2009095635 A2 | 5/2009 |
| JP | 2010233998 A2 | 10/2010 |
| JP | 2011045673 A2 | 3/2011 |
| JP | 2011072431 A2 | 4/2011 |
| JP | 2011209749 A2 | 10/2011 |
| WO | 2004072687 A2 | 8/2004 |

OTHER PUBLICATIONS

Extended European Search Report issued on Jan. 27, 2016 for the corresponding EP Patent Application No. 13813519.9.

* cited by examiner

*FIG. 8*
(a)
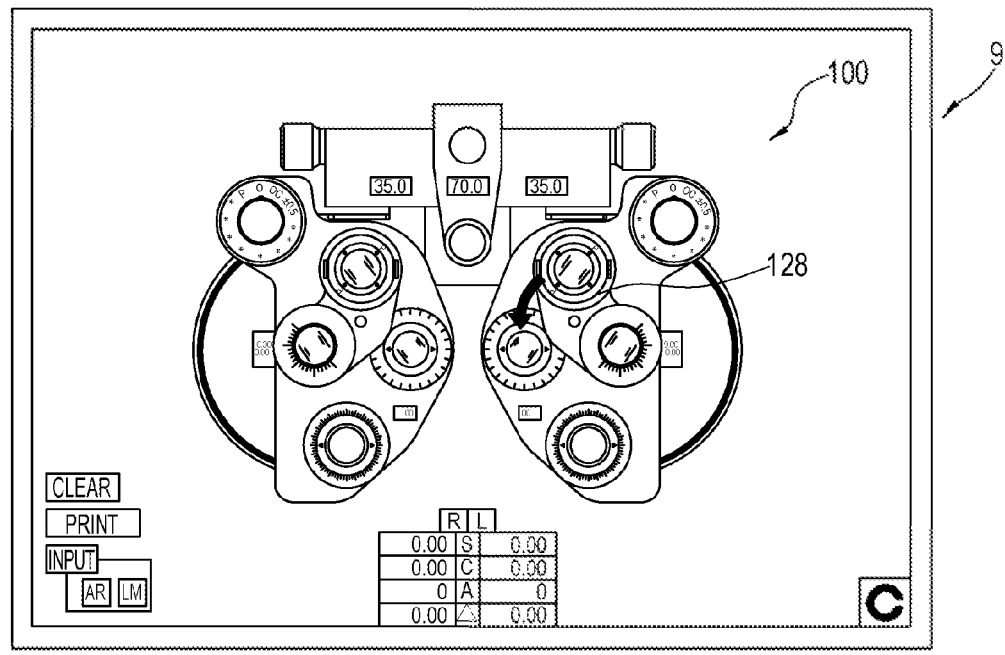
(b)
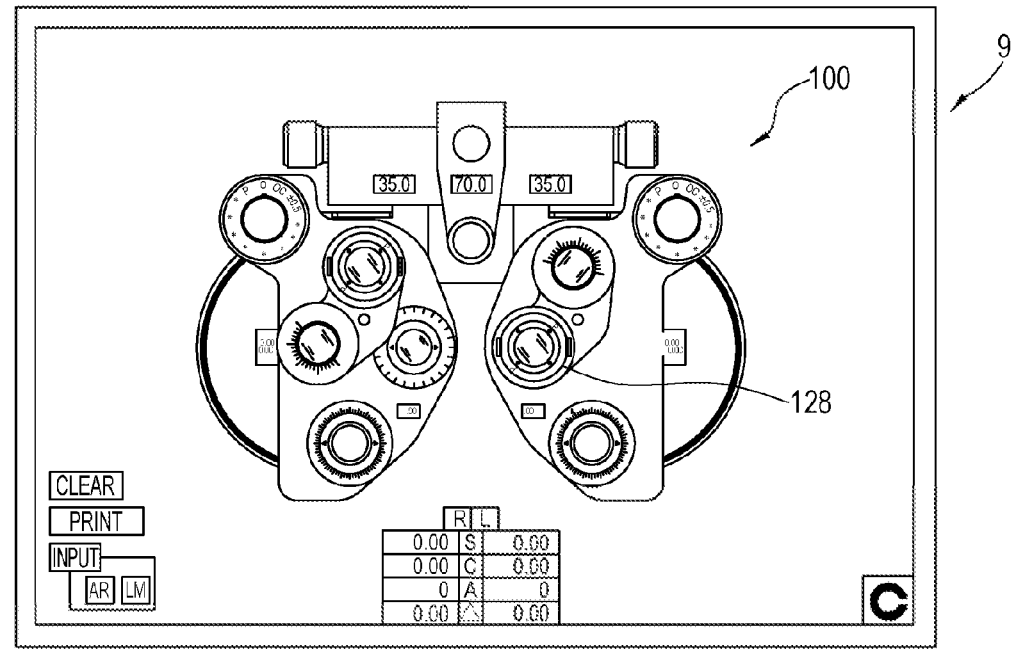

*FIG. 9*
(a)
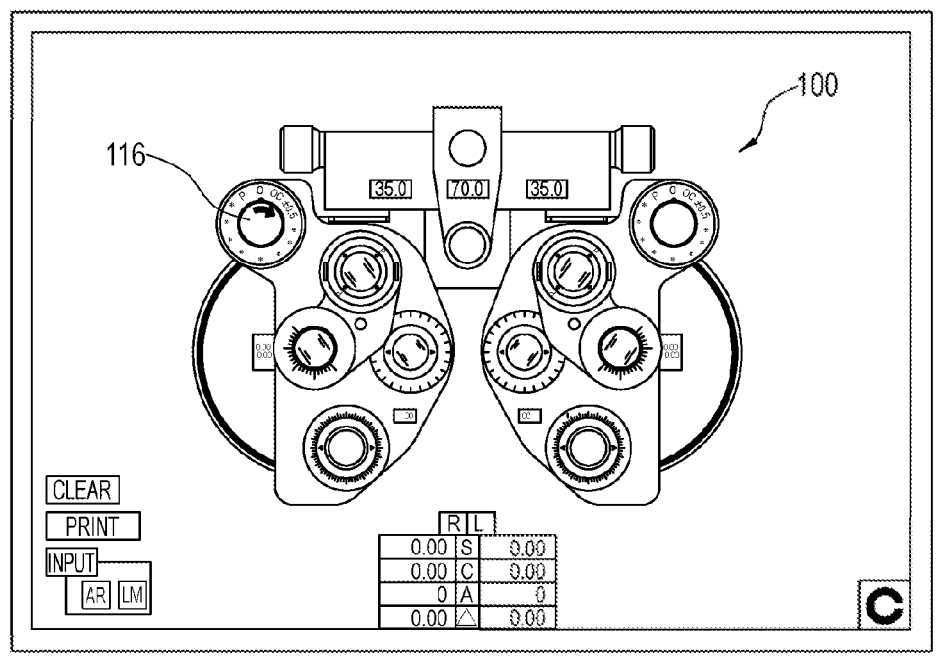
(b)
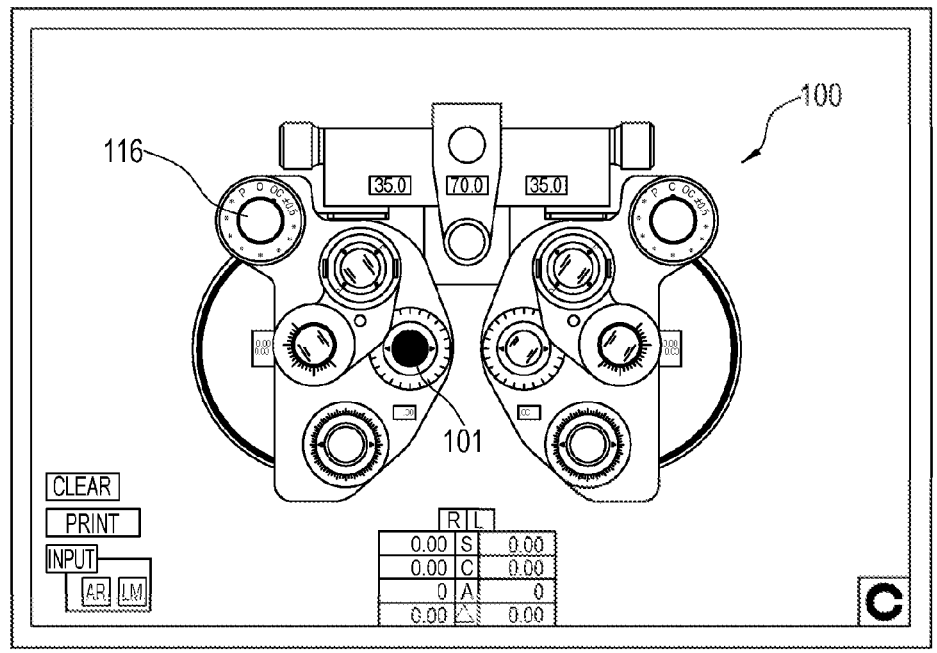

FIG. 10
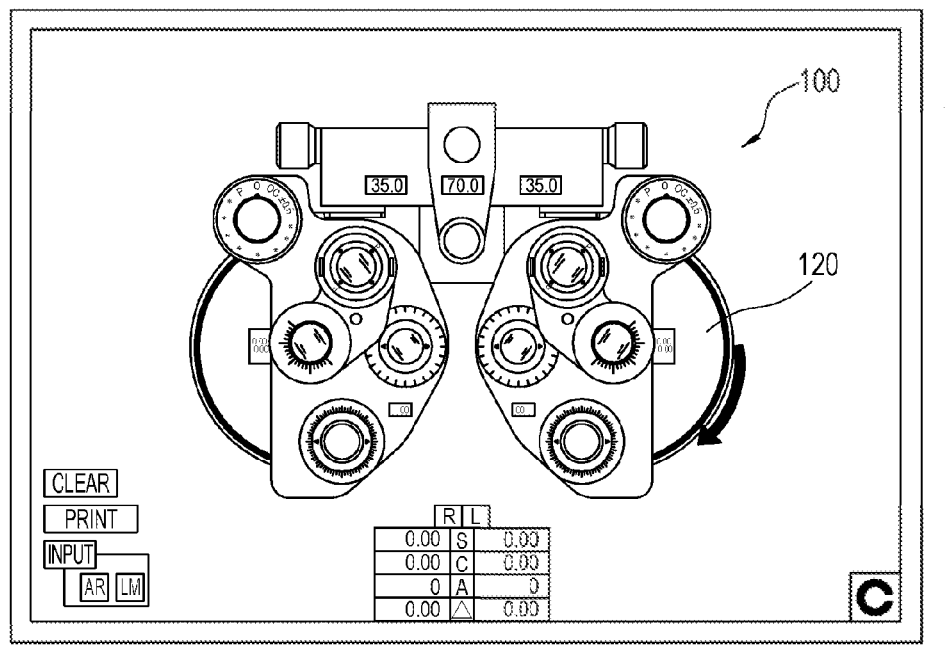
(a)
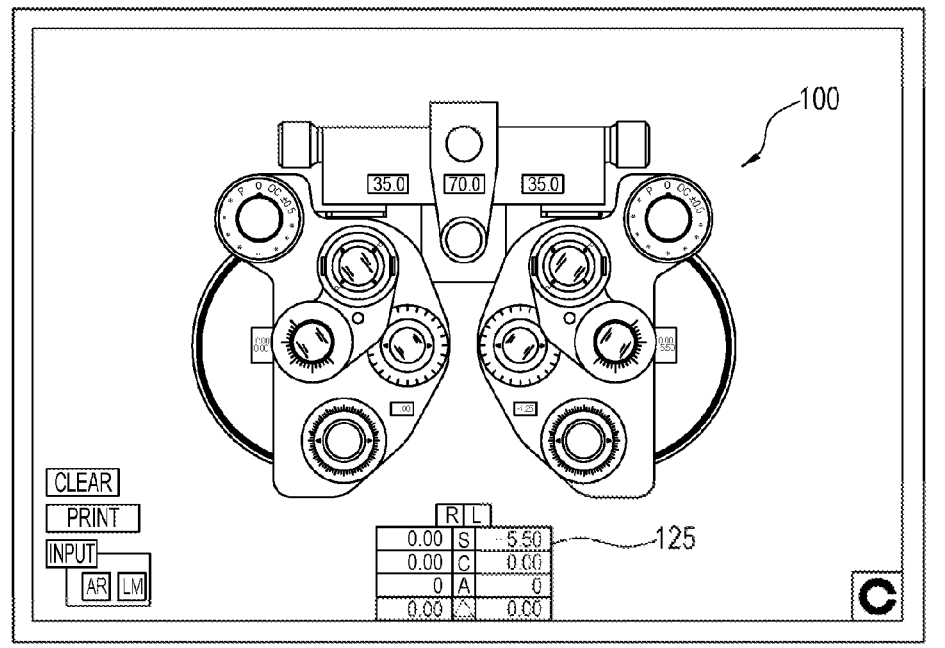
(b)

FIG. 11
(a)
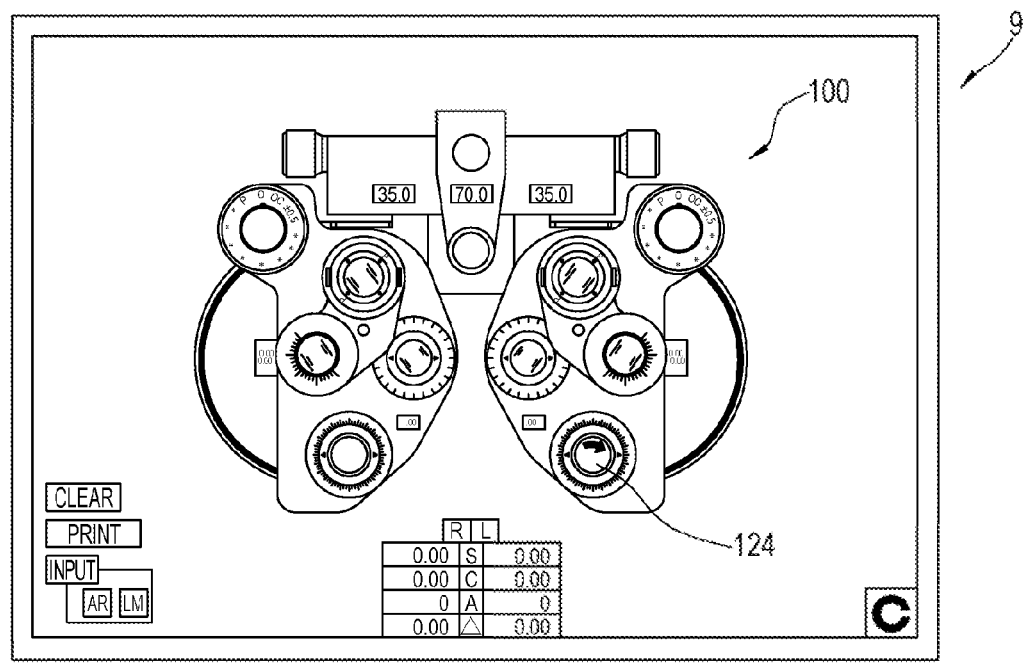
(b)
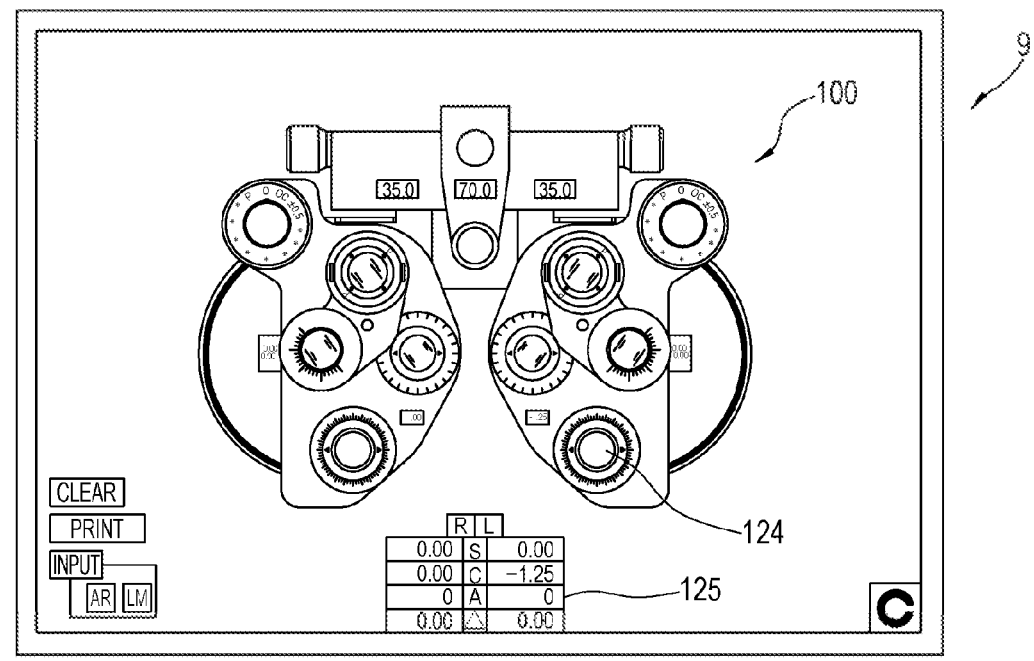

FIG. 18
(a)
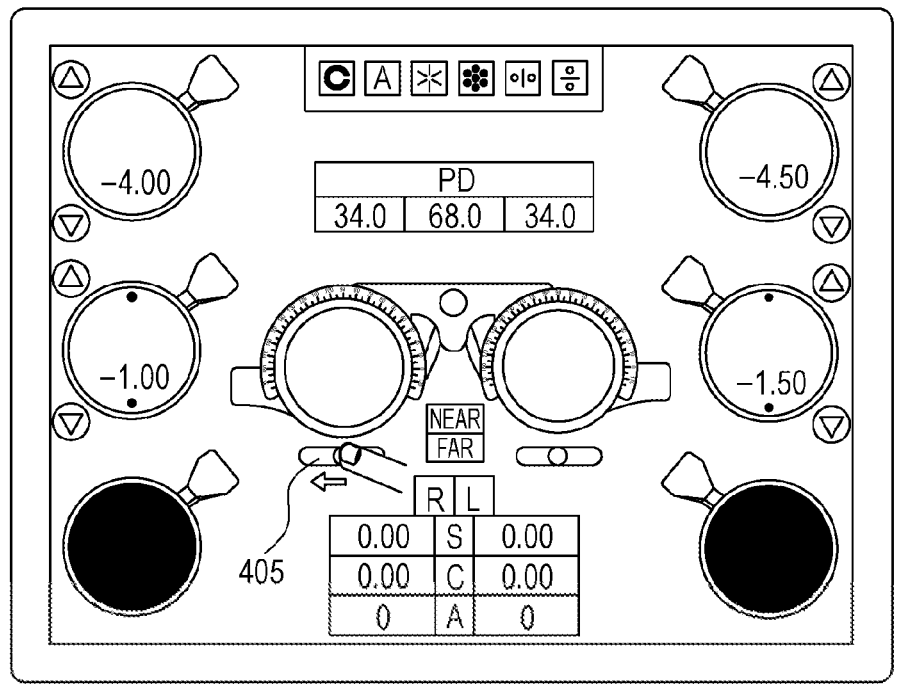
(b)
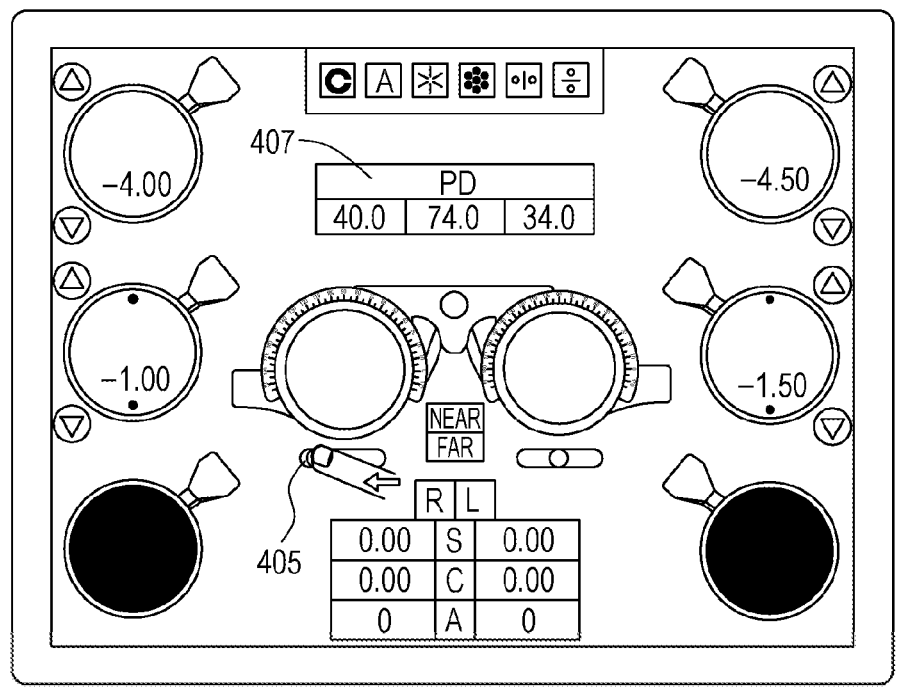

FIG. 19
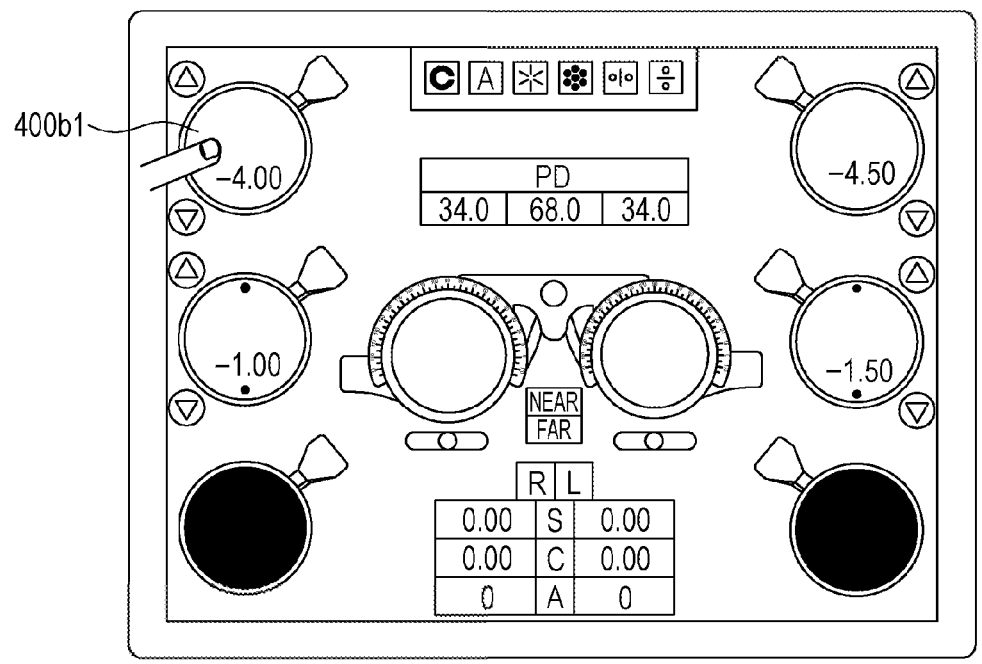
(a)
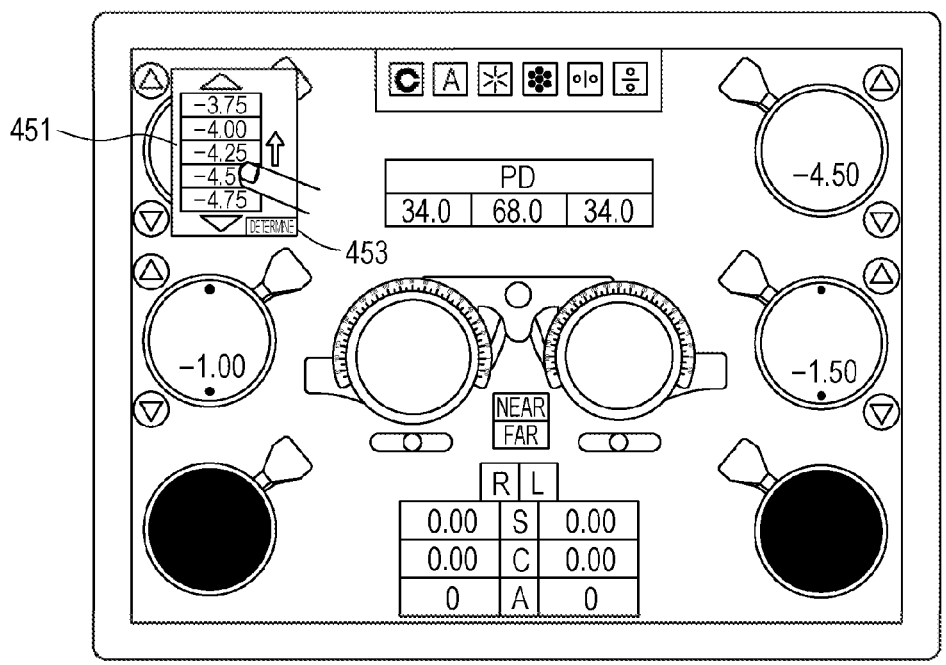
(b)

FIG. 20
(a)
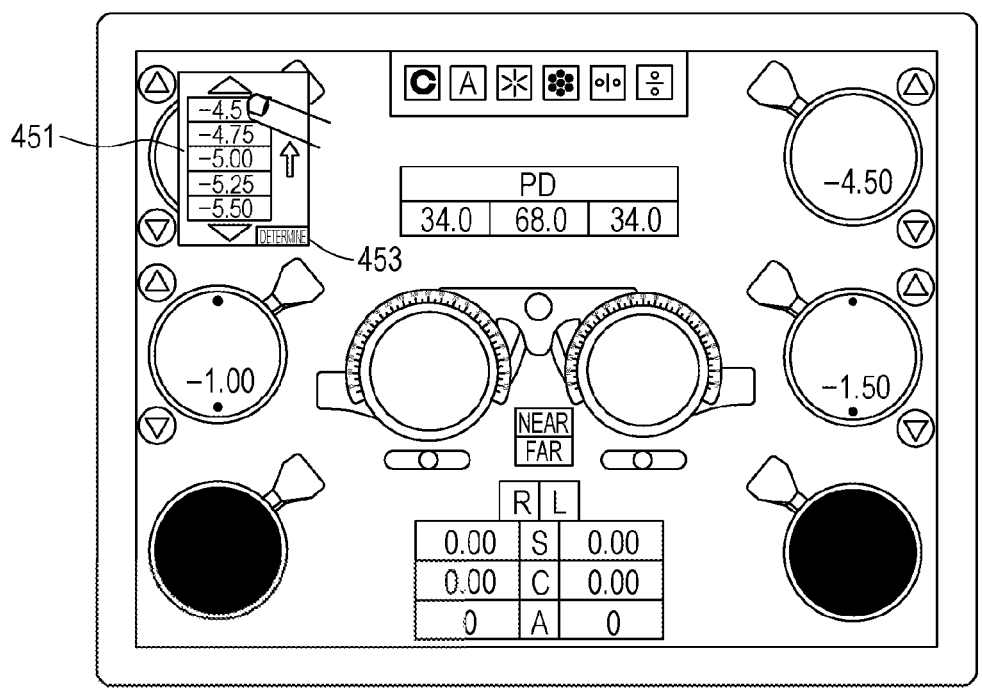
(b)
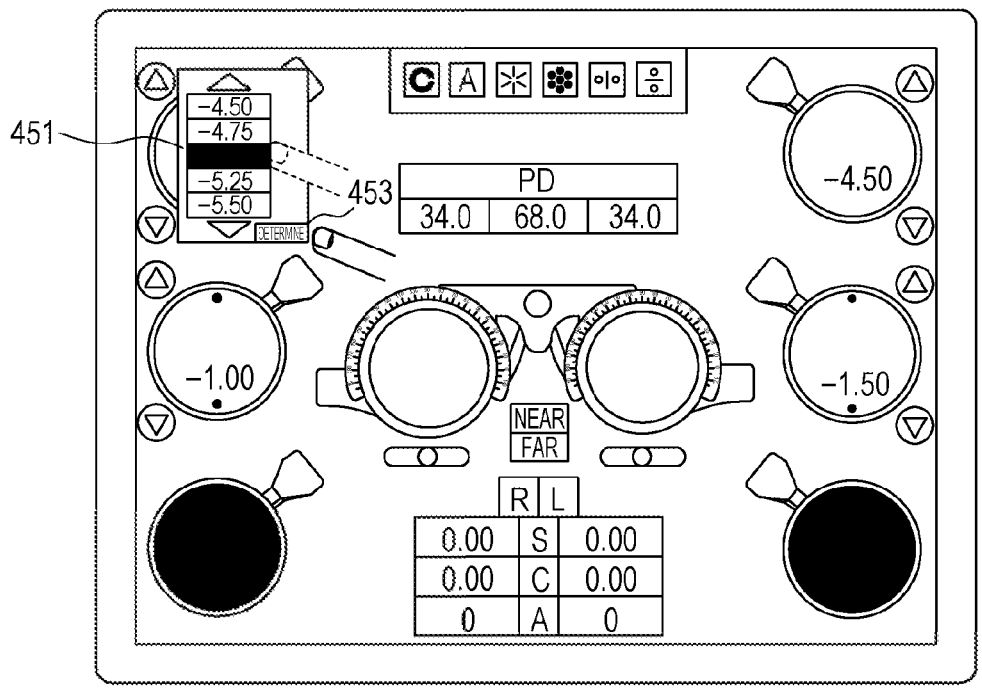

FIG. 21
(a)
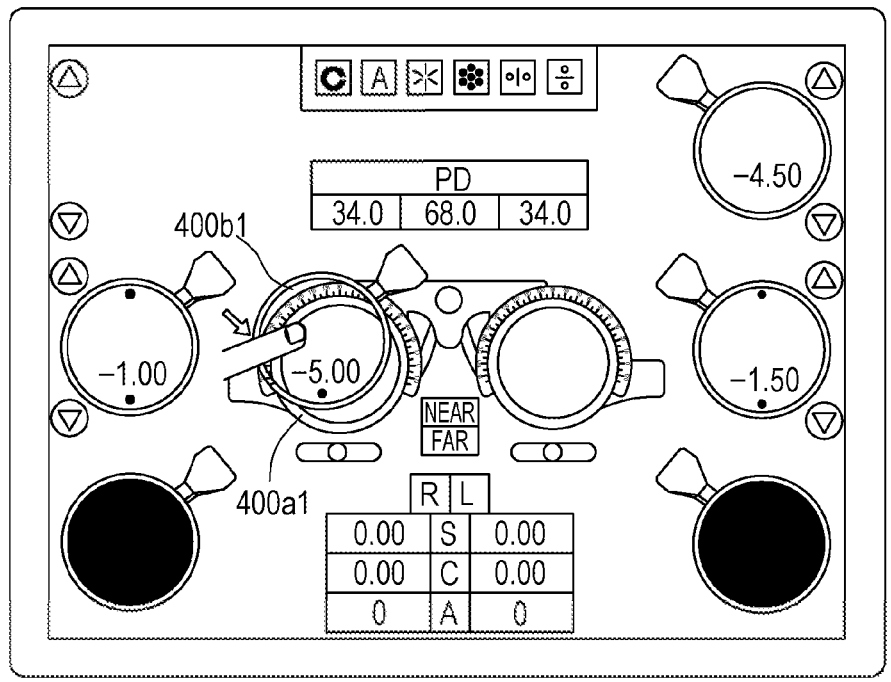
(b)
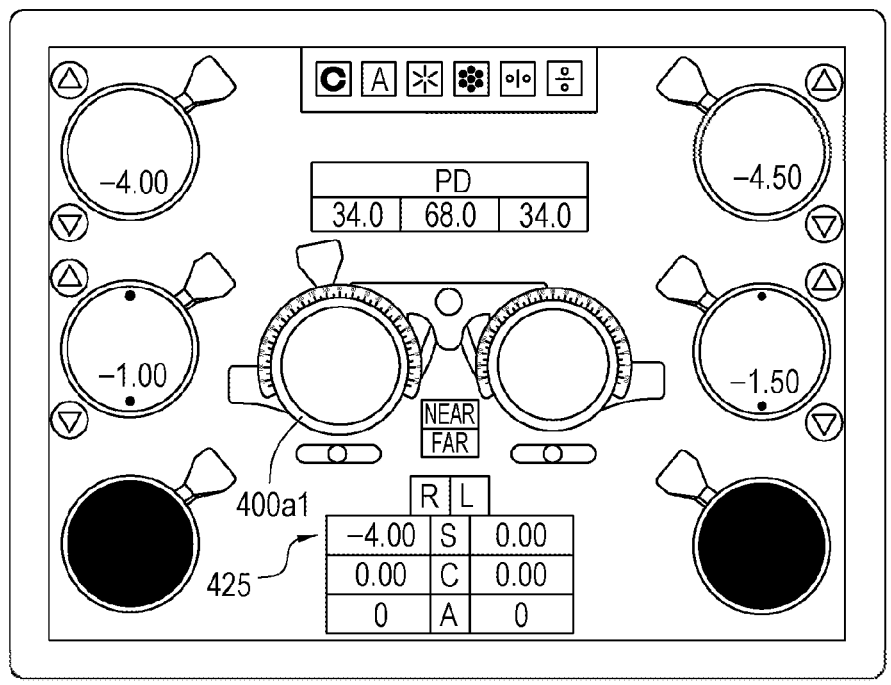

FIG. 22
(a)
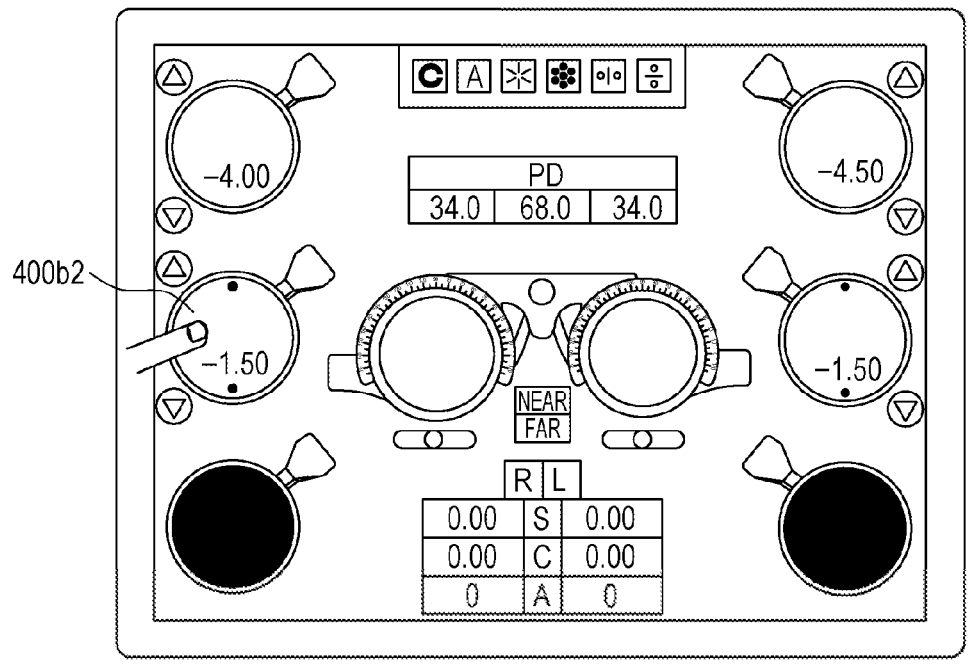
(b)
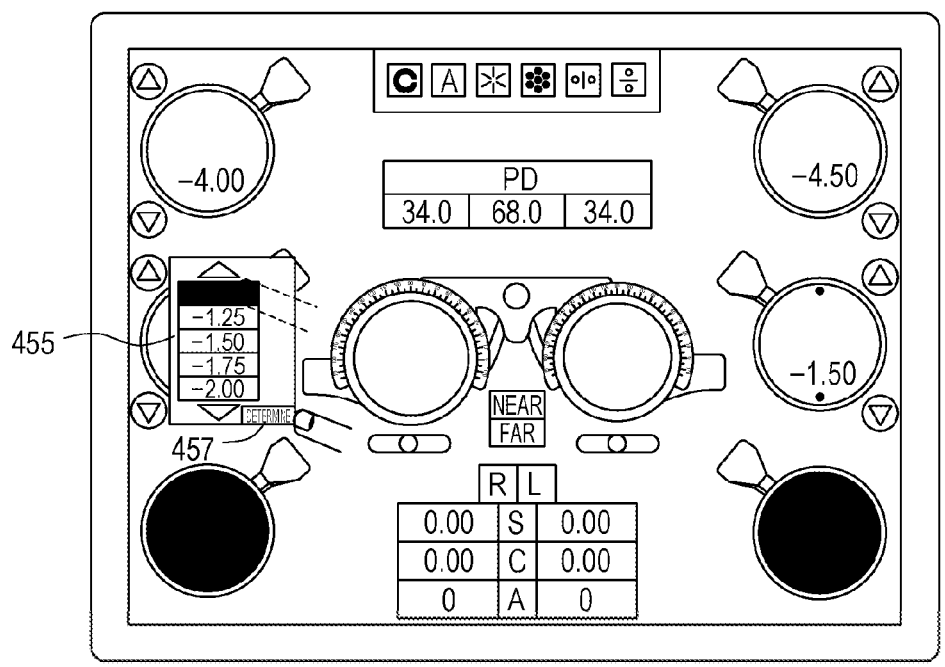

FIG. 23
(a)
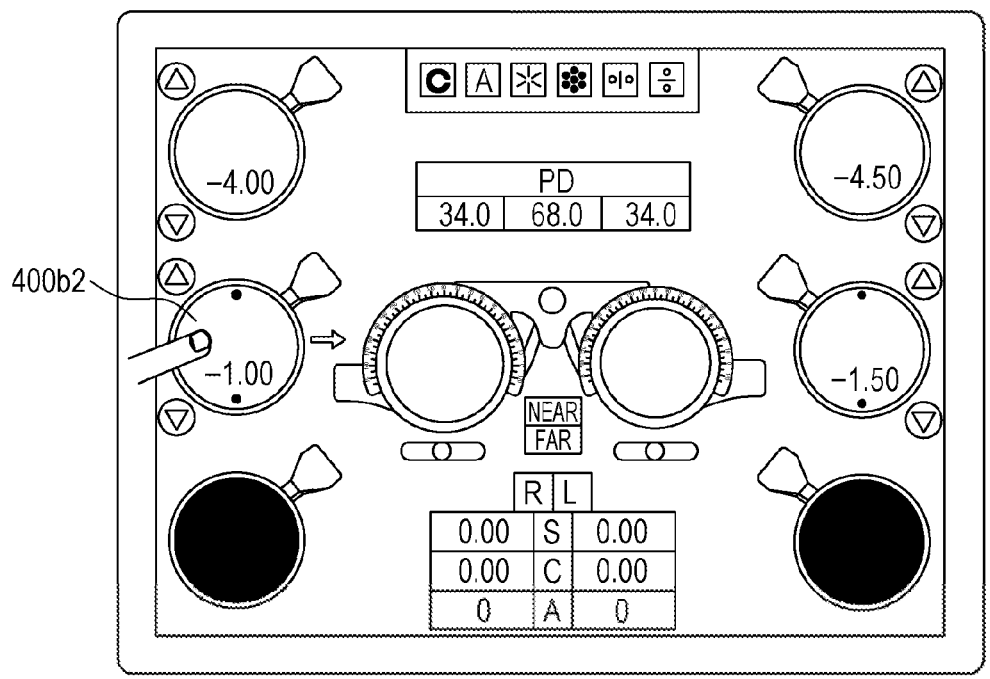
(b)
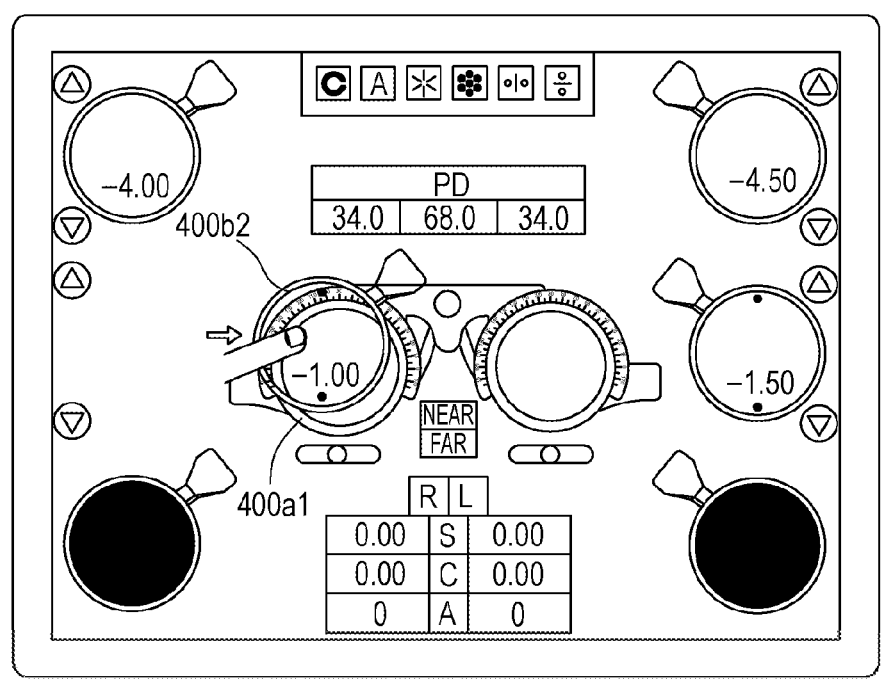

FIG. 24
(a)
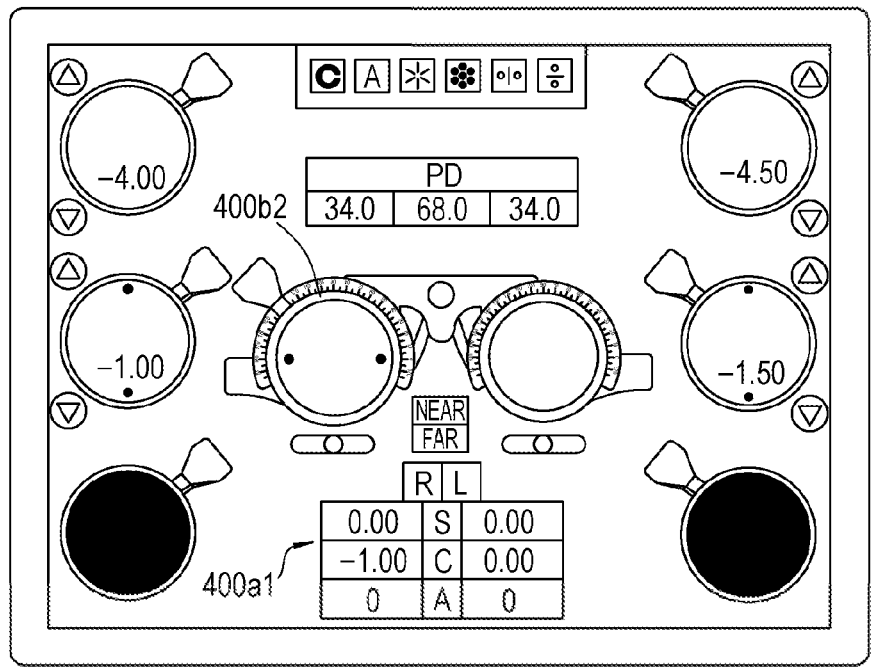
(b)
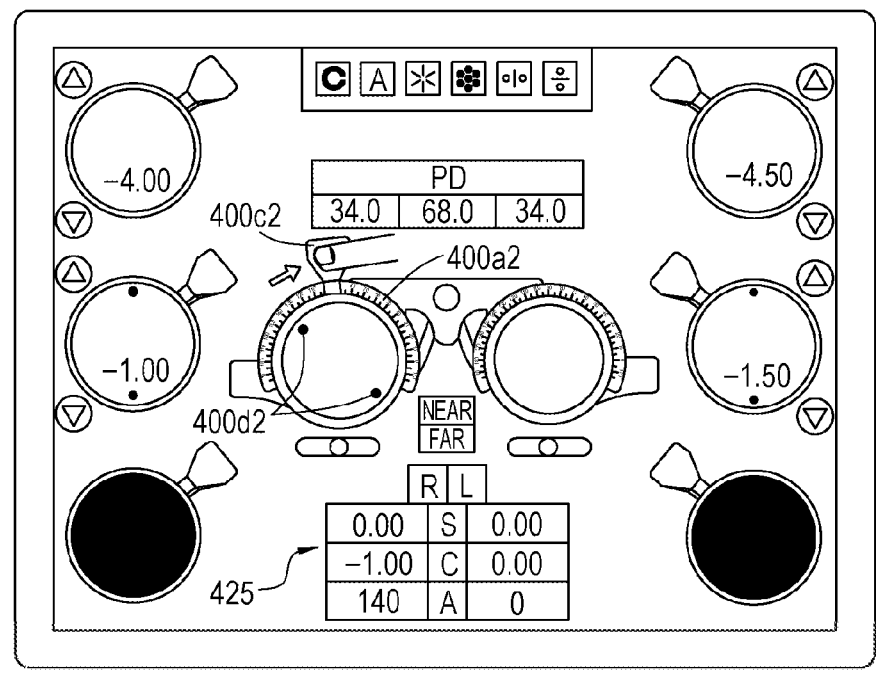

FIG. 25
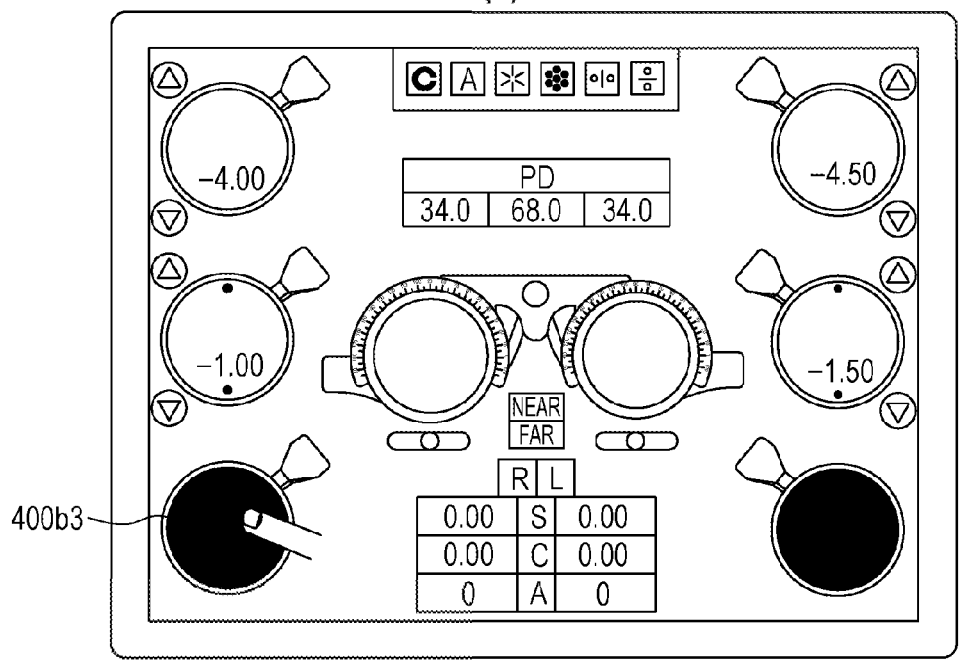
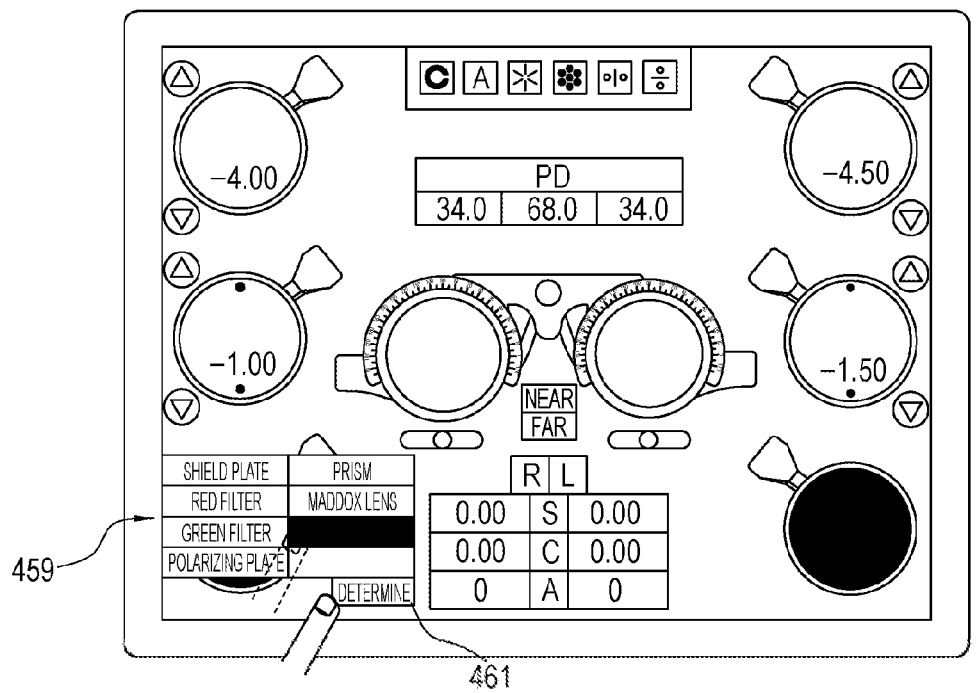

FIG. 26
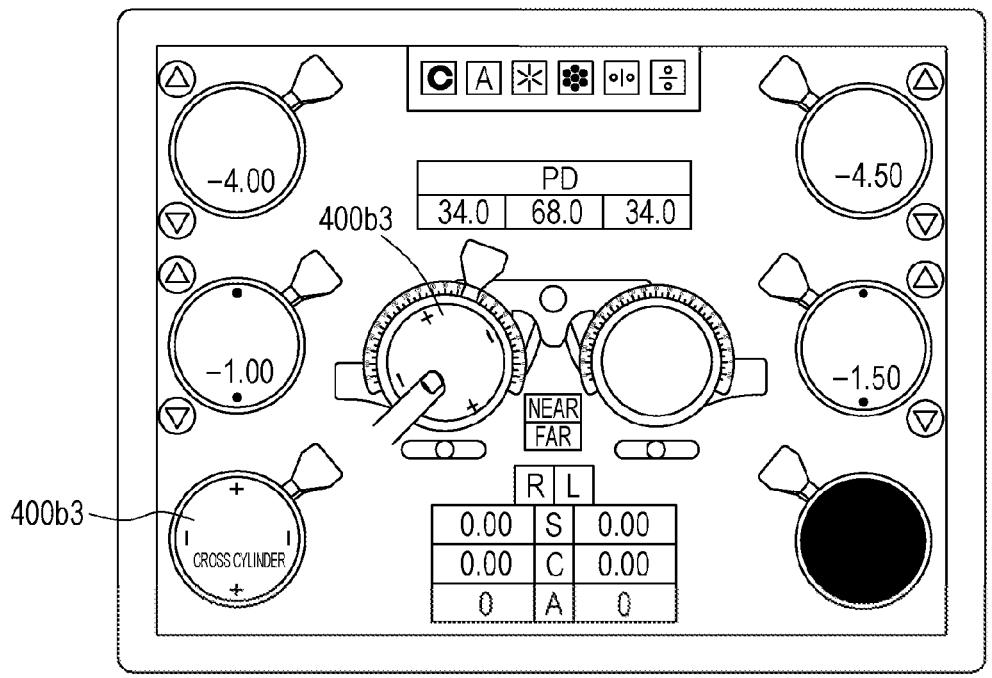
(a)
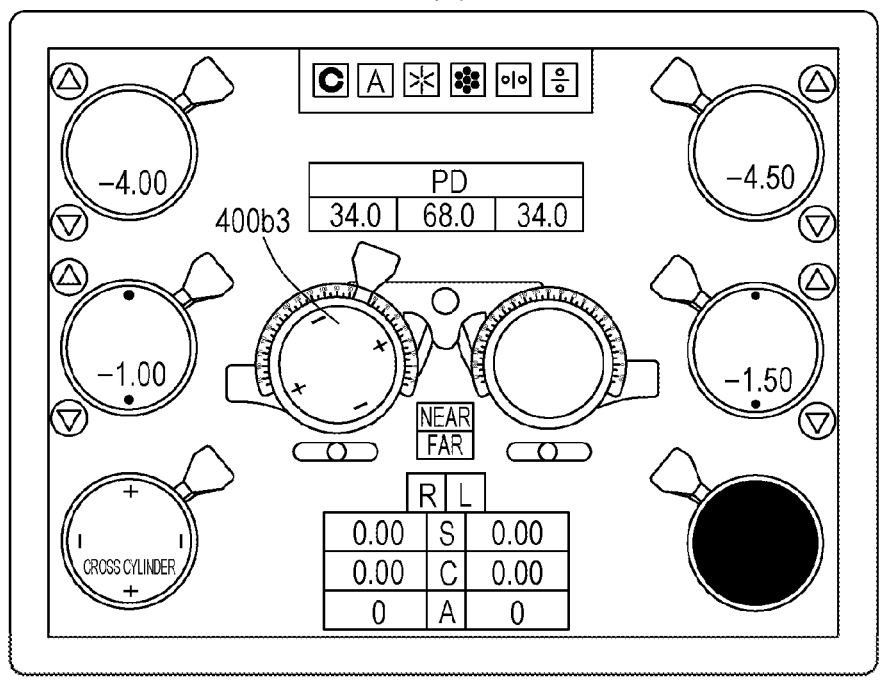
(b)

OPTOMETRY APPARATUS CONTROLLER, OPTOMETRY SYSTEM, AND STORAGE MEDIUM HAVING OPTOMETRY APPARATUS PROGRAM STORED THEREIN

TECHNICAL FIELD

The present invention relates to an optometry apparatus controller for operating an optometry apparatus main body, an optometry system equipped with the same, and a storage medium having an optometry apparatus program stored therein.

BACKGROUND ART

A subjective optometry apparatus (a so-called electric refractor) is known which includes a pair of left and right lens units with optometry windows disposed therein, and in which a lens disc is electrically rotated. The apparatus is operated by an attached controller. When a lens diopter power and the like are input into the controller by an examiner, the lens and the like provided in the optometry apparatus main body are electrically switched (see Patent Document 1). The conventional controller includes a base provided with various switches (rotation knobs, push buttons), and a display disposed in the optometry apparatus for displaying optical characteristics.

Meanwhile, as a subjective optometry apparatus, a manual optometry apparatus (a so-called manual refractor) is known. In the manual optometry apparatus, the lens disposed in the examination window is switched by the examiner rotating a rotation knob, a disc and the like provided in a lens chamber unit of the optometry apparatus (see Patent Document 2).

CITATION LIST

Patent Literatures

Patent Document 1: JP-A-2011-072431
Patent Document 2: JP-A-2011-045673

SUMMARY OF INVENTION

Problems to be Solved by the Invention

The manual refractor and the conventional electric refractor greatly differ in device operation method. Thus, it has been difficult for an examiner used to the manual refractor to handle the controller of the electric refractor. Namely, the examiner who has been using the manual refractor needs a lot of time in order to become used to the operation.

In view of the above problem of the conventional technology, a technical object of the present invention is to provide an optometry apparatus controller, an optometry system, and an optometry apparatus program, enabling the examiner who is not used to the electric refractor to easily operate the electric refractor.

Solutions to the Problems

In order to achieve the object, the present invention is characterized by the following configurations.

(1) In an optometry apparatus controller provided in an electric optometry apparatus including an optical element disposed in front of an examinee's eye and a switch mechanism that electrically switches the optical element, for instructing the switching of the optical element, the controller includes a touchscreen configured to display an operation screen for operating the electric optometry apparatus main body, displays, as the operation screen, a graphic image of a manual optometry apparatus as viewed from an operator side, the manual optometry apparatus including a plurality of operating units and being configured to switch the optical element disposed in front of the eye by an operation with respect to the operating units, and outputs a control signal to the electric optometry apparatus main body based on a touch input with respect to the graphic image on the touchscreen.

(2) A storage medium having stored therein an optometry apparatus program causes a computer with a touchscreen to function as an optometry apparatus controller for providing an instruction for switching an optical element of an optometry apparatus main body including the optical element disposed in front of an examinee's eye and a switch unit that electrically switches the optical element. The program causes the computer to function as: a touch input detection unit that detects a touch input from the touchscreen; a display control unit that causes an operation screen for operating the optometry apparatus main body to be displayed on the touchscreen, the display control unit causing a graphic image of a manual refractor as viewed from the operator side to be displayed as the operation screen, the manual refractor including a lens chamber unit and a plurality of rotating operating units provided in the lens chamber unit, and being configured to mechanically switch the optical element disposed in front of the eye by a rotating operation with respect to the plurality of rotating operating units; and an output unit that outputs a control signal to the optometry apparatus main body based on the touch input with respect to the graphic image on the touchscreen.

(3) An optometry system for examining an examinee's eye includes: the optometry apparatus controller according to (1); and an optometry apparatus main body including an optical element disposed in front of an examinee's eye and a switch unit that electrically switches the optical element.

Effects of the Invention

According to the present invention, the examiner who is not used to the electric refractor can easily operate the electric refractor.

DESCRIPTION OF THE EMBODIMENTS

<First Embodiment>

A first embodiment of the present invention will be described with reference to the drawings. FIG. 1 is a schematic diagram illustrating an optometry system as a whole according to the present embodiment. FIG. 2 is a schematic exterior diagram of an optometry apparatus according to the present embodiment as viewed from the examinee. FIG. 3 is a control system block diagram of the present embodiment. FIG. 4 illustrates an example of a lens disc according to the present embodiment.

<Optometry Apparatus Main Body>

An optometry apparatus main body 1 includes a pair of left and right symmetric lens chamber units (optometry units) 60, and a movable unit 6 supporting the left and right lens chamber units 60 in a suspended manner. In the lens chamber units 60, lens discs 64 are rotatably held (see FIG. 2). In the lens discs 64, a number of optical elements (a spherical lens, a cylindrical lens, a dispersing prism and the like) are disposed on the same circumference. The lens discs 64 are rotation-controlled by driving parts (actuators) 50 to dispose an optical element desired by the examiner in optometry windows 61. The optical element (such as the cylindrical lens, the cross cylinder lens, or the rotary prism) disposed in the optometry windows 61 is rotation-controlled by a driving part 51 to dispose the optical element at a rotation angle desired by the examiner. The optical element disposed in the optometry windows 61 are switched by operating a controller 9 as an input unit (operation unit). The driving pans 50 for rotating the lens discs 64 include a driving source. Examples of the driving source include a motor and a solenoid. However, the driving source is not limited to such examples. The mechanism of the driving parts 50 may include a well-known configuration.

The lens discs 64 include one lens disc or a plurality of lens discs, as illustrated in FIG. 4. When a plurality of lens discs is disposed, driving parts 50*a* to 50*f* corresponding to each lens disc are provided. For example, as a lens disc group, each lens disc is provided with an opening (or a 0 D lens) and a plurality of optical elements. Representative examples of each lens disc include a spherical lens disc having a plurality of spherical lenses with different diopter powers, a cylindrical lens disc having a plurality of cylindrical lenses with different diopter powers, and an auxiliary lens disc. In the auxiliary lens disc, at least one of a red filter/green filter, a prism, a cross cylinder lens, a polarizing plate, a Maddox lens, and an auto cross cylinder lens is disposed. The cylindrical lens is disposed rotatably by a driving part 51*a* about an optical axis L1. The rotary prism and the cross cylinder lens are disposed rotatably by driving parts 51*b* and 51*c* about the optical axis L1. For detailed configuration of the lens disc mechanism, reference may be made to JP-A-2007-68574 and JP-A-2011-72431, for example.

The movable unit 6 includes a driving part 52 (FIG. 3) with a slide mechanism. The slide mechanism adjusts the interval of the left and right lens chamber units 60. The movable unit 6 changes the interval of the optometry windows 61 in accordance with the pupillary distance of the examinee. The movable unit 6 also includes a driving part 53 with a convergence mechanism. The convergence mechanism adjusts the convergence angle (inset angle) of the left and right lens chamber units 60. For detailed configuration of the movable unit, reference may be made to JP-A-2004-329345, for example.

A forehead rest 70 that abuts the forehead of the examinee is linked with the movable unit 6 by a link portion 71. The forehead rest 70 has the role of holding the examinee's head and affixing the position of the examinee's eye at a predetermined examination position.

A support column 3 is mounted to the table 10. To the support column 3, a support arm 5 is movably attached. The support arm 5 supports the optometry apparatus main body 1 over the table 10. The support arm 5 can be moved up and down using a switch 11, which is an up/down switch. Using the switch 11, the height position of the support arm can be adjusted and the height of the optometry apparatus main body 1 can be adjusted via drive unit, which is not illustrated.

The optometry apparatus main body 1 is not limited to the above configuration. The optometry apparatus main body 1 may have any configuration capable of electrically switching the optical element disposed in front of the examinee's eye. For example, the configuration may be such that the diopter power is switched by driving an electric active lens (see JP-A-2011-209749).

<Target Presenting Device>

A target presenting device 20 is provided with a target presenting unit 21 that presents a distance-examination target. The target presenting device 20 is connected to the controller 9 (preferably wirelessly) via a relay unit 12. Switching and the like of the target displayed on the display 31 are performed by operating the controller 9.

The target presenting device 20 displays the examination target on the target presenting unit 21 in accordance with an operation signal input from the controller 9. The target presenting device 20 is located at substantially the same height and installed so as to be away from the optometry apparatus main body 1 by a distance suitable for examination. According to the present embodiment, the distance between the optometry apparatus main body 1 and the target presenting device 20 (examination distance, installation distance) is adapted for distance-examination, such as 5 m. The target presenting device 20 is not limited to the illustrated display. As the target presenting device 20, there may be used a chart projector that projects the target on a screen, or a space-saving type target project device that projects the target via a concave mirror.

To the movable unit 6, a rod 2 is attached. To the rod 2 is attached a near target presenting unit 4 movably in a longitudinal direction of the rod, the near target presenting unit 4 with a near chart having a plurality of examination targets drawn thereon. FIG. 1 and FIG. 2 illustrate the state in which the rod 2 is folded with the near target presenting unit 4 flipped upward. During near-examination, the rod 2 is horizontally oriented, with the near target presenting unit 4 placed at a predetermined position from the device main body 1. The position can be adjusted to a desired distance from the examinee's eye.

<Controller>

The controller 9 is a tablet computer for operating at least one of the optometry apparatus main body 1 and the target presenting device 20. The controller 9 is not affixed to the table 10 and can be carried by the examiner as needed. The controller 9 includes a display panel 30 with touchscreen function to detect an operation on the display panel 30 by the examiner. The controller 9 outputs a drive signal to the optometry apparatus main body 1 and the target presenting device 20 based on the operation by the examiner. The controller 9 is used for providing instruction for switching the optical element disposed in front of the eye, for example.

The system of the touchscreen is not particularly limited. For example, one of an electrostatic touchscreen, a pressure-sensitive touchscreen, and an optical touchscreen may be used.

As illustrated in FIG. 3, a control part 204 functions as a main constituent for the implementation of the controller 9. As the control part 204, the CPU of the tablet computer is used, for example. The control part 204 executes various processes in accordance with a program for controlling the optometry apparatus main body 1 and the target presenting device 20. The program is stored in a storage medium, such as a storage part 210 provided in the tablet computer. The storage medium may be a CD-ROM or a flash memory, for example. In this case, the control part 204 may execute the program stored in the connected CD-ROM or flash memory.

The touchscreen of the controller 9 includes a touchscreen configured to display an operation screen for operating the optometry apparatus main body 1.

The controller 9 displays the graphic image 100 relating to the manual optometry apparatus as the operation screen. The controller 9 also outputs a control signal to the optometry apparatus main body 1 based on the touch input to the graphic image 100 on the touchscreen.

On the display panel 30, the graphic image 100 relating to the manual optometry apparatus is displayed (see FIG. 5). The graphic image 100 is an image of the manual optometry apparatus as viewed from the examiner. In the present embodiment, the manual optometry apparatus displayed as the graphic image 100) is a manual refractor. The manual refractor refers to a device that includes manual type lens chamber units and a plurality of rotating operating units provided in the lens chamber units, and that mechanically switches the optical member disposed at the examinee's eye by a rotating operation with respect to the rotating operating units. The rotating operating units include at least one of a rotation knob and a rotating disc, for example, and are disposed on the examiner-side anterior surface and lateral surface of the lens chamber units. The manual type lens chamber units are generally configured to be disposed in a left-right pair. The examiner side herein refers to the side on which the plurality of rotating operating units is provided in the manual optometry apparatus. Namely, the examiner side is the side of the operator who operates the plurality of rotating operating units.

The graphic image 100 may be a graphic image depicting the lens chamber units of the manual optometry apparatus, or a graphic image based on an actually taken image of the lens chamber units of the manual optometry apparatus.

For example, when the rotating operating units of the graphic image 100 are operated, the driving of the optometry apparatus main body 1 is controlled in accordance with the operation. In the controller 9, an angle sensor, which is not illustrated, is disposed as a screen direction detection unit. The display image on the display panel 30 is automatically switched to normal orientation in accordance with the direction of the controller 9. The display screen of the display panel 30 is presented in a correct upper-lower and left-right state as the display panel 30 is rotated (so that the image information is not shown laterally rotated or upside down). In this regard, the control part 204 detects the monitor direction based on a detection signal from the angle sensor. Based on the signal, the control part 204 controls the display of the image information on the display panel 30. At the same time, the control part 200 rotates the position coordinates of the buttons on the touchscreen to fix the apparent location of the touchscreen buttons before and after rotation of the display panel 30.

<Relay Unit>

The relay unit 12 is a unit that controls power supply of the optometry apparatus main body 1 and communication from the controller 9 to the optometry apparatus main body 1 and the target presenting device 20. The relay unit 12 is connected to the controller 9, the optometry apparatus main body 1, and the target presenting device 20. The connection may be wireless or wired. The relay unit 12 is provided with a control part 200 including a CPU and the like. The relay unit 12 controls the optometry apparatus main body 1 and the target presenting device 20 in response to a control instruction from the controller 9.

Preferably, the exchange of signals between the relay unit 12 and the controller 9 may be performed by wireless communication. The system of communication may include Wi-Fi (registered trademark Wi-Fi). Bluetooth (registered trademark Bluetooth) and the like. However, the communication system is not limited to these and may be adopted from various systems. The relay unit 12 is not necessarily a required element. The optometry apparatus main body 1 and the target presenting device 20 may be configured to receive the control instruction from the controller 9.

FIG. 6 is a flowchart for describing an example of control for driving the driving parts 50 and 51 of the lens chamber units by an operation on the touchscreen.

In the touchscreen display panel 30, two-dimensional coordinate axes (x-axis and y-axis) are set by a program in advance. From the different coordinates (x, y), different signals are transmitted. Thus, a position designated on the display panel 30 (designated point) is recognized by the control part 204.

In the storage part 210, there are also stored in advance drive amounts for the driving parts 50 and 51 per unit coordinate. The control part 204 determines, from the difference in the x-axis component and the y-axis component per unit time when the designated point is dragged, the amount of movement of the lens chamber units 60 in the respective areas (such as the amount of rotation of the lens disc, and the amounts of rotation of the cylindrical lens, the rotary prism, and the cross cylinder lens), and calculates the drive amount of each of the driving parts 50 and 51.

When the device is started, the control part 204 reads, constantly or at predetermined time intervals, a signal transmitted from the display panel 30 (step 301), and performs analysis as to whether there is a signal from the display panel 30 (step 302). When the display panel 30 is not pressed, no signal is detected from the display panel 30. Thus, the process returns to step 301, and the control part 204 repeats the reception for a voltage signal.

When the display panel 30 is pressed, the control part 204 recognizes the coordinates (position) of the designated point based on the signal transmitted from the display panel 30 (step 303). As long as the state in which the display panel 30 is pressed continues, the signal is continuously transmitted from the display panel 30. The control part 204 compares the coordinates detected based on the received signal at unit time basis, and determines whether there is a movement of the designated point on the display panel 30 (step 304).

Then, the control part 204 determines the amount and direction of movement when the designated point is dragged (step 305). The control part 204, in accordance with the determined amount and direction of movement, transmits a signal for moving each area of the lens chamber units 60 to the respective driving parts 50 and 51 (step 306).

After completion of step 306, the process returns to step 301. Thereafter, based on a change in the coordinates of the designated point detected at each subsequent detection time (t2, t3, . . . ), the calculation of the amount of rotation or the amount and direction of movement is repeated.

When the pressing at the designated point on the display panel 30 is released and reception of the signal from the display panel 30 ceases, the control pan 204 recognizes that the finger has been released from the designated point (step 302). Then, of the signals transmitted from the display panel 30, the coordinates that have been last detected are stored in the storage part 210 as the final position (step 310). Here, the coordinates at a designated point P2 (such as the coordinates (x100, y100) detected at time t100) are stored in the storage pan 210.

The control part 204 then calculates the direction and amount of movement based on the coordinates stored last and the coordinates detected from the preceding signal (step 311). At this time, the control part 204 checks the remaining amount of the drive amount for each of the driving parts 50 and 51. If there is a remaining amount of the drive amount of each for the driving parts 50 and 51, a new drive signal to which the amount of movement calculated in step 311 is added to the remaining amount is transmitted to each driving part (steps 313 and 314).

The control part 204 monitors to see if there is a remaining amount in the drive amount for each of the driving parts 50 and 51. If there is a remaining amount, the control part 204 causes the driving of each driving part to continue (steps 315 and 316). When the remaining amount of the drive amount becomes zero, the control part 204 causes the driving of each driving part to stop (step 317). By the signal processing from steps 310 to 317, the control part 204 can track the position to which the designated point is finally dragged, and cause each area of the lens chamber units 60 to be moved and rotated, even when the dragging speed on the display panel 30 is too fast.

As described above, the optometry apparatus main body 1 is driven in operative association with the movement of the manual optometry apparatus displayed on the display panel 30 by dragging. Thus, the examiner can implement the examination by an intuitive operation.

For example, in response to an operation with respect to the rotating operating units of the graphic image 100 (such as a spherical disc 120), the controller 9 causes the rotating operating units displayed on the graphic image 100 to be rotated (see FIG. 5 and FIG. 10).

For example, the controller 9 forms on the graphic image 100 a display region (such as a cylindrical lens scale 122b or an information display portion 125) that displays the optical characteristics of the optical element of the optometry apparatus main body 1 disposed in front of the examinee's eye (see FIG. 5).

For example, the display region includes a scale (such as a cylindrical lens scale 122b) formed outside the rotating operating units of the graphic image 100 (such as an astigmatic axis conversion knob 122). On the rotating operating units of the graphic image 100 (for example, on the astigmatic axis conversion knob 122), a reference mark (such as reference mark ST) is formed (see FIG. 5). The controller 9 displays the rotating operating units of the graphic image (100 so as to be moved with respect to the scale (such as the cylindrical lens scale 122b) in accordance with an operation with respect to the rotating operating units of the graphic image 100) (such as the astigmatic axis conversion knob 122).

FIG. 5 illustrates an example of the display screen of the display panel 30 according to the present embodiment. In the present embodiment, with regard to the layout of the graphic image 100), the lens chamber units 100a are displayed in a left-right pair so as to provide an operation feel similar to that of the manual optometry apparatus. Over the lens chamber units 100a, a movable unit 100b is displayed. The movable unit 100b corresponds to the element of the manual optometry apparatus for moving the left and right lens chamber units.

The layout of the lens chamber units 100a will be described with reference to the lens chamber unit 100 on the right side of the screen as an example (corresponding to the lens chamber unit for the left eye). The disc-shaped spherical disc 120 is displayed with a left-side half thereof covered by a lens chamber unit main body 102. The disc-shaped spherical disc 120 is displayed with a right half thereof exposed to the outside. A spherical diopter power display portion 120a is displayed at the center of the spherical disc 120. On the left side of the lens chamber unit main body 102, an optometry window 101 is displayed. To the lower right of the optometry window 101, the astigmatic axis conversion knob 122 and the cylindrical power conversion knob 124 are displayed. The cylindrical power conversion knob 124 and the astigmatic axis conversion knob 122 are concentrically disposed. The cylindrical power conversion knob 124 is formed on the inside, and the astigmatic axis conversion knob 122 is formed on the outside. Near the cylindrical power conversion knob 124 and the astigmatic axis conversion knob 122, a cylindrical power display portion 124a is formed. To the upper right of the optometry window 101, a turret 132 is displayed. In the turret 132, a cross cylinder unit 128 and a rotary prism unit 140 are formed. To the upper right of the turret 132, an auxiliary lens knob 116 is displayed. The auxiliary lens knob 116 is concentrically disposed with a spherical degree fast-forward dial 121, with the auxiliary lens knob 116 disposed on the inside and the spherical degree fast-forward dial 121 disposed on the outside.

Description of the lens chamber unit 100 on the screen left side (corresponding to the right eye lens chamber unit) will be omitted as the unit is left-right symmetric with respect to the lens chamber unit 100 on the right side of the screen.

The layout of the lens chamber units 100a is not limited to the above display mode and may be set in accordance with the required examination purpose. For example, when the layout is such that at least the spherical disc 120, the optometry window 101, the astigmatic axis conversion knob 122, and the cylindrical power conversion knob 124 are displayed, the spherical diopter power and the cylindrical power of the examinee's eye can be measured. Such layout may also be configured so that, depending on the purpose of use, the cross cylinder unit 128, the rotary prism unit 140, the auxiliary lens knob 116 and the like can be additionally displayed.

The layout of the movable unit 100b will be described. At each of the left and right ends of the movable unit 100b, a pupillary distance (PD) adjusting knob 105 is displayed. A right eye PD display portion 104R and a PD display portion 104L are displayed in the vicinity of the respective adjusting knob 105. A binocular PD display portion 104 is displayed at the center of the movable unit 100b. A near/far switching button 137 is displayed at the center of the movable unit 100b. A forehead rest lamp 112 is displayed in the space between the left and right lens chamber units 100a.

An information display portion 125 is displayed in a peripheral portion of the screen (such as below). The information display portion 125 displays the optical characteristics (such as the lens diopter power and a prism value) of the optical element disposed in front of the examinee's eye in the optometry apparatus main body 1. A target chart selection button 127 is displayed in a peripheral portion of the screen (such as at the lower right), and used for selecting the target presented by the target presenting device 20.

A method of operating the controller 9 using the graphic image 100 will be described. In the display panel 30, a signal for driving the driving parts 50 to 53 of the optometry apparatus main body 1 is input by the touch of the examiner's finger (or a stylus). In the graphic image 100, a plurality of operating units (rotating operating units) for driving the optometry apparatus main body 1 is formed. The spherical disc 120, the spherical degree fast-forward dial 121, the astigmatic axis conversion knob 122, the cylindrical power conversion knob 124, the turret 132, the cross cylinder unit 128, the rotary prism unit 140, the auxiliary lens knob 116, and the PD (pupillary distance) adjusting knob 105 are respectively used as the operating units on the graphic image 100.

When at least one of the rotating operating units on the graphic image 100 is dragged by the examiner, a drive signal corresponding to the dragged operating unit is output to the optometry apparatus main body 1. The drive signal includes, for example, drive information about the direction and amount of movement of at least one device element of the optometry apparatus main body 1. The optometry apparatus main body 1 drives the driving parts (50 to 53) in accordance with the signal from the controller 9.

Here, the control part 204 identifies, from the plurality of operating units displayed on the graphic image 100, one operating unit in accordance with the coordinate position touched on the touchscreen. The control part 204 then determines the direction of operation with respect to the identified operating unit, and detects the amount of operation of the operating unit based on the trajectory of operation. The control part 204 transmits to the optometry apparatus main body 1 a drive signal corresponding to the direction and amount of operation at the identified operating unit.

Specifically, the drive signal is sent from the controller 9 to the control part 202 of the optometry apparatus main body 1 via the relay unit 12. The control part 202 identifies, from the plurality of driving parts 50 to 53, the driving part corresponding to the drive signal from the controller 9. The control part 202 controls the identified driving part in a drive direction and with a drive amount corresponding to the direction and amount of operation on the controller 9.

For example, the amount of movement of each portion of the lens chamber units 60 is determined by the amount of movement (drag amount) of the designated point touched by the finger. Then, in accordance with the speed of movement (drag speed) of the designated point touched by the finger, the speed of movement of each portion of the lens chamber units 60 is determined. For example, when the examiner moves the designated point fast so as to rotate the operating unit on the graphic image 100 fast, the device element of the optometry apparatus main body 1 corresponding to the operated operating unit is moved fast.

It should be noted that the driving parts 50 and 51 of the optometry apparatus main body 1 may not be necessarily directly driven in accordance with the direction and amount of operation on the graphic image 100 in the controller 9. For example, the control part 204 of the controller 9 may determine the optical element to be disposed in the optometry window 62 of the lens chamber units 60 in accordance with the direction and amount of operation on the controller 9, and then transmit to the optometry apparatus main body 1 a drive signal for disposing the determined optical element in the optometry window 62. Based on the drive signal, the control part 202 of the optometry apparatus main body 1 controls the driving parts 50 and 51 so that the determined optical element can be disposed in the optometry window 62. Similar setting may be made for the driving of the driving parts 52 and 53 in accordance with an operation signal from the controller 9.

In the following, the operation corresponding to each operating unit will be described. FIG. 7(a) illustrates the controller 9 prior to operating the PD adjusting knob 105. When the PD adjusting knob 105 is rotated in the direction of the arrow, the distance between the lens chamber units becomes smaller, as illustrated in FIG. 7(b). FIG. 8(a) illustrates the controller 9 prior to operating the turret 132. When the turret 132 is rotated in the direction of the arrow, the cross cylinder 130 is set in the optometry window 101, as illustrated in FIG. 8(b). FIG. 9(a) illustrates the controller 9 prior to operating the auxiliary lens knob 116. When the auxiliary lens knob 116 is rotated in the direction of the arrow and the scale is set for the occluder "OC", the optometry window 101 is blocked, as illustrated in FIG. 9(b). FIG. 10(a) illustrates the controller 9 prior to operating the spherical disc 120. When the spherical disc 120 is rotated in the direction of the arrow, the corresponding numerical value in the information display portion 125 is switched, as illustrated in FIG. 10(b). FIG. 11(a) illustrates the controller 9 prior to operating the cylindrical power conversion knob 124. When the cylindrical power conversion knob 124 is rotated in the direction of the arrow, the corresponding numerical value in the information display portion 125 is switched, as illustrated in FIG. 11(b).

Specifically, referring mainly to FIG. 2, FIG. 3, and FIG. 5, when the finger touches the PD adjusting knob 105 and operates the PD adjusting knob 105 up or down, the PD adjusting knob 105 is rotated in the upper or lower direction, whereby the distance between the left and right lens chamber units 100a is adjusted. The controller 9 reads the direction and amount of operation of the PD adjusting knob 105, and transmits a drive signal to the control part 202. The control part 202 controls the driving part 52 to adjust the distance between the left and right optometry windows 61. In the right eye PD display portion 104R, the binocular PD display portion 104, and the PD display portion 104L on the display panel 30, the distances of the left and right optometry windows 61 are displayed. When the distances of the left and right optometry windows 61 are modified, the control part 204 displays information corresponding to the information corresponding to the modified distances.

When a pressure is applied to the forehead rest 70 of the device main body 1, a pressure detection part 203 included in the forehead rest 70 detects the pressure and sends a signal to the control part 202 of the optometry apparatus main body 1. An instruction signal from the control part 202 is sent to the control part 204 of the controller 9 via the control part 200 of the relay unit 12. Based on a detection result from the pressure detection part 203, the control part 204 controls the forehead rest lamp 112 on the graphic image 100. For example, when the forehead of the examinee is properly affixed onto the forehead rest 70, the lamp 112 is turned off. When the forehead of the examinee is not properly affixed onto the forehead rest 70, the lamp 112 is turned on. Obviously, the lamp 112 may be configured to be turned on when the forehead of the examinee is properly affixed onto the forehead rest 70 and turned off when the forehead of the examinee is not properly affixed onto the forehead rest 70.

When the finger touches the auxiliary lens knob 116 and rotates the auxiliary lens knob 116 in the circumference direction thereof, the auxiliary lens knob 116 is rotated in the operated direction. The auxiliary lens knob 116 is rotated relative to the auxiliary lens scale 118. The examiner, referring to the auxiliary lens scale 118 on the auxiliary lens knob 116, selects a desired auxiliary lens. The controller 9 reads the direction and amount of operation with respect to the auxiliary lens knob 116, and transmits a drive signal to the control part 202. The control pan 202 controls the driving parts 50 to dispose the auxiliary lens corresponding to the display of the auxiliary lens scale 118 in the optometry window 61.

When the finger touches the spherical disc 120 and rotates the spherical disc 120 in the circumference direction thereof, the spherical disc 120 is rotated in the operated direction. As the spherical disc 120 is rotated, the display of the spherical diopter power in the spherical diopter power display portion 120a and the information display portion 125 is modified in accordance with the direction and amount of operation. The examiner, referring to the spherical diopter power display portion 120a, the information display portion 125 and the like, disposes a desired spherical lens in the optometry window 61. The controller 9 reads the direction and amount of operation with respect to the spherical disc 120, and transmits a drive signal to the control part 202. The control part 202 controls the driving part 50 to dispose the spherical lens corresponding to the display of the spherical diopter power display portion 120a (or the information display portion 125) in the optometry window 61. By the above operation, the spherical diopter power is converted in predetermined steps (such as in 0.25 D or 0.5 D step).

When the finger touches the spherical degree fast-forward dial 121 and rotates the spherical degree fast-forward dial 121 in the circumference direction thereof, the spherical degree fast-forward dial 121 is rotated in the operated direction. As the spherical degree fast-forward dial 121 is rotated, the display of the spherical diopter power in the spherical diopter power display portion 120a and the information display portion 125 is modified in accordance with the direction and amount of operation. The examiner, referring to the spherical diopter power display portion 120a, the information display portion 125 and the like, disposes a desired spherical lens in the optometry windows 61. The controller 9 reads the direction and amount of operation with respect to the spherical degree fast-forward dial 121, and transmits a drive signal to the control part 202. The control part 202 controls the driving part 50 to dispose the spherical lens corresponding to the display of the spherical diopter power display portion 120a (or the information display portion 125) in the optometry window 61. By the above operation, the spherical diopter power is converted in larger steps than the steps of the spherical disc 120 (for example, in 2.0 D or 3.0 D steps).

When the finger touches the astigmatic axis conversion knob 122 and rotates the astigmatic axis conversion knob 122 in the circumference direction thereof, the astigmatic axis conversion knob 122 is rotated in the operated direction. The astigmatic axis conversion knob 122 is rotated relative to the cylindrical lens scale 122b. As the astigmatic axis conversion knob 122 is rotated, the display of the astigmatic axis in the information display portion 125 is modified in accordance with the direction and amount of operation. The examiner, referring to the cylindrical lens scale 122b on the astigmatic axis conversion knob 122, the information display portion 125 and the like, adjusts the axis of the cylindrical lens. The controller 9 reads the direction and amount of operation with respect to the astigmatic axis conversion knob 122, and transmits a drive signal to the control part 202. The control part 202 controls the driving part 51 to adjust the astigmatic axis of the cylindrical lens disposed in the optometry window 61.

When the finger touches the cylindrical power conversion knob 124 and rotates the cylindrical power conversion knob 124 in the circumference direction thereof, the cylindrical power conversion knob 124 is rotated in the operated direction. As the cylindrical power conversion knob 124 is rotated, the display of the cylindrical power in the cylindrical power display portion 124a and the information display portion 125 is modified in accordance with the direction and amount of operation. The examiner, referring to the cylindrical power display portion 124a, the information display portion 125 and the like, disposes the desired astigmatism lens in the optometry windows 61. The controller 9 reads the direction and amount of operation with respect to the cylindrical power conversion knob 124, transmits a drive signal to the control part 202.

The control part 202 controls the driving part 50 to dispose the astigmatism lens corresponding to the display of the cylindrical power display portion 124a and the information display portion 125 in the optometry window 61. By the above operation, the cylindrical power is converted in predetermined steps (such as in 0.25 or 0.5 D steps).

When the finger touches the turret 132 and rotates the turret 132 about the rotation axis 132b, one of the cross cylinder unit 128 and rotary prism unit 140 is disposed in the optometry window 101 on the display panel 30 in accordance with the rotation direction. The controller 9 reads the operated direction with respect to the turret 132, and transmits a drive signal to the control part 202. The control pan 202 controls the driving part 50 to dispose the cross cylinder lens or the rotary prism in the optometry window 61.

When the cross cylinder unit 128 is set in the optometry window 101, as the finger touches the cross cylinder unit 128 and rotates the cross cylinder unit 128 in the circumference direction thereof, the cross cylinder unit 128 is rotated in the operated direction. The examiner, referring to the scale on the cross cylinder unit 128, can adjust the axial angle of the cross cylinder 130. The controller 9 reads the direction and amount of operation with respect to the cross cylinder unit 128, and transmits a drive signal to the control part 202. The control part 202 controls the driving part 51 to adjust the astigmatic axis of the cross cylinder lens disposed in the optometry windows 61.

When the cross cylinder knob 134 is touched and operated by the finger, the cross cylinder 130 is displayed as inverted with respect to the operated direction. The examiner, referring to the P mark 136 on the cross cylinder unit 128, can control the astigmatic axis. The controller 9 reads the inversion operation by the cross cylinder knob 134 with respect to the cross cylinder 130, and transmits a drive signal to the control part 202. The control part 202 controls the driving part 51 to invert the astigmatic axis of the cross cylinder lens.

When the rotary prism unit 140 is set in the optometry window 101, as the rotary prism unit 140 is touched by the finger and the rotary prism unit 120 is rotated in the circumference direction thereof, the rotary prism unit 140 is rotated in the operated direction. The rotary prism unit 140 is rotated relative to the rotary prism scale 140a. As the rotary prism unit 120 is rotated, the display of the prism amount in the information display portion 125 is modified in accordance with the direction and amount of operation. The examiner, referring to the rotary prism scale 140a, the information display portion 125 and the like, adjusts the prism amount of the rotary prism. The controller 9 reads the direction and amount of operation with respect to the rotary prism unit 140, and transmits a drive signal to the control part 202. The control part 202 controls the driving part 51 to adjust the prism amount of the rotary prism disposed in the optometry windows 61.

When the examiner desires to switch the presented target, the examiner touches a desired target chart button formed on the screen from the target chart selection button 127. When the target chart selection button 127 is touched, the control part 204 detects which switch has been touched.

In the target chart selection button 127, a plurality of various targets is displayed. When the desired target is touched with the finger, the target is selected. The selected target is selectively displayed on the display panel 30 (for example, the display color is inverted). The controller 9 transmits a control signal for presenting the selected target to the examinee to the control part 206. The control part 206 controls the target presenting unit 21 to present the selected target to the examinee.

In the above configuration, the examiner can operate the electric optometry apparatus by handling the controller with an operation interval similar to that of the manual optometry apparatus. Thus, the examiner who is used to the manual optometry apparatus and not the electric optometry apparatus can easily operate the electric optometry apparatus.

<Eyesight Measurement>

The case in which an eyesight measurement is performed using the controller 9 will be concretely described. When there is a pupillary distance PD obtained with an objective eye refractive power measurement apparatus, which is not illustrated, the examiner inputs the pupillary distance PD into the optometry apparatus main body 1.

The control part 202 controls the driving part 52 for a distance corresponding to the input pupillary distance PD, and adjusts the interval of the optometry windows 61. When the pupillary distance PD is not present, or when the pupillary distance PD that is set is to be modified, the examiner operates the PD adjusting knob 105 to adjust the distance between the left and right optometry windows 61.

<Eyesight Check>

An eyesight checking method will be described. First, the right eye examination is performed. The auxiliary lens knob 116 is rotated and, while looking at the auxiliary lens scale 118, the right eye is set to open "O" and the left eye is set to occluder "OC". The control part 202, based on an operation signal from the controller 9, controls the driving parts 50 to open the right-side optometry window while closing the left-side optometry window.

When there is objective measurement data (spherical diopter power S, cylindrical power C, astigmatic axis angle A) obtained with the objective eye refractive power measurement apparatus (not illustrated), the examiner inputs the objective measurement data to the optometry apparatus main body 1. The control part 202 controls the driving parts 50 and 51 so that an optical element corresponding to the input objective measurement data is disposed. Obviously, previous spectacles data obtained with a lens meter may be used.

On the other hand, when the objective measurement data is absent, a prospective diopter power assumed from the uncorrected vision is entered by rotating the spherical disc 120. Then, the astigmatic axis degree is entered by rotating the astigmatic axis conversion knob 122 and the cylindrical power conversion knob 124.

When the spherical diopter power of the lens disposed in the optometry windows 61 is modified, the spherical disc 120 is rotated in the circumference direction while being touched to display a desired numerical value in the spherical diopter power display portion 120a and the information display portion 125. The control part 202, based on the operation signal from the controller 9, rotates the lens discs 64 so as to cause the lens of the spherical diopter power corresponding to the displayed numerical value to be disposed in the optometry windows 61. The examiner may use the spherical diopter power fast-forward dial 121 as needed.

When the cylindrical power of the lens disposed in the optometry windows 61 is modified, the cylindrical power conversion knob 124 is rotated in the circumference direction while being touched so as to cause a desired numerical value to be displayed in the cylindrical power display portion 124a and the information display portion 125. The control part 202, based on an operation signal from the controller 9, rotates the lens discs 64 so that the lens of a cylindrical power corresponding to the displayed numerical value is disposed in the optometry windows 61.

When the astigmatic axis angle of the cylindrical lens disposed in the optometry windows 61 is modified, the cylindrical power conversion knob 124 is rotated in the circumference direction while being touched to cause a desired numerical value to be displayed in the information display portion 125. The control part 202, based on an operation signal from the controller 9, rotates the lens discs 64 so that the cylindrical lens is disposed in the astigmatic axis corresponding to the displayed numerical value.

<Red-Green Test>

Next, the target chart button 126 is touched to display the target chart selection button 127. When the target for eyesight 0.5 in the display chart 126 is touched, the control part 206, based on an operation signal from the controller 9, presents the target for eyesight 0.5 to the examinee's eye. When the target for eyesight 0.5 can be discerned, the examination proceeds to the red-green test.

A red-green test method will be described. First, the examiner touches the target chart button 126 to display the target chart selection button 127. When the red-green chart in the target chart selection button 127 is touched, the control part 206, based on an operation signal from the controller 9, presents a red-green chart to the examinee's eye. Then, the examiner rotates the spherical disc 120 to add plus 0.5 to the spherical diopter power displayed in the spherical diopter power display portion 121. The control part 202, based on an operation signal from the controller 9, controls the driving parts 50 to add a spherical lens of plus 0.5.

The examiner then confirms whether a red ring or a green ring is more clearly visible, and adjusts the spherical diopter power. If the red ring is clearly visible, the spherical disc 120 is rotated to add −0.25 D. If the green ring is clearly visible, the spherical disc 120 is rotated to add +0.25 D. This procedure is repeated until the red chart and the green chart are equally clearly visible.

<Measurement of Astigmatic Axis>

An astigmatic axis measurement method will be described. First, the target chart button 126 is touched to display the target chart selection button 127, and then a point-group chart in the target chart selection button 127 is touched. The control part 206, based on an operation signal from the controller 9, presents the point-group chart to the examinee's eye. Then, the turret 132 is rotated to set the cross cylinder 130 in the optometry window 101. The control part 202, based on an operation signal from the controller 9, controls the driving parts 50 to set the cross cylinder in the optometry windows 61.

The examiner then rotates the cross cylinder unit 128 to align the rotation axis of the cross cylinder 130 with the astigmatic axis. When the astigmatic axis shown on the astigmatic axis conversion knob 122 and the astigmatic axis of the cross cylinder 130 are aligned, the controller 9 makes an informing display to that effect (such as by blinking the cross cylinder 130 or changing its color). The control part 202, based on an operation signal from the controller 9, controls the driving part 51 to cause the cross cylinder to be disposed in the designated rotation axis in the optometry windows 61.

When the examiner rotates the cross cylinder knob 134 to invert the cross cylinder 130, the control part 202, based on an operation signal from the controller 9, controls the driving part 51 to invert the astigmatic axis of the cross cylinder.

Here, the visibility to the examinee is confirmed. On the cross cylinder 130, a red point 130R and a white point 130W are formed. The examiner rotates the astigmatic axis conversion knob 122 in the direction of the red point 130R on a clearly visible surface to convert the astigmatic axis angle by a predetermined amount (such as 15°). When reversing, the knob is reversed in steps smaller than the predetermined steps. The control part 202 controls the driving part 51 based on an operation signal from the controller 9 to adjust the astigmatic axis angle of the optical element. The examiner repeats the above until the visibility is substantially the same before and after inverting the cross cylinder.

<Measurement of Cylindrical Power>

A cylindrical power measurement method will be described. First, the target chart button 126 is touched to display the target chart selection button 127, and the point-group chart in the target chart selection button 127 is touched. The control part 206 presents the point-group chart to the examinee's eye based on an operation signal from the controller 9. Then, the turret 132 is rotated to set the cross cylinder 130 in the optometry window 101. Based on an operation signal from the controller 9, the control part 202 controls the driving parts 50 to set the cross cylinder in the optometry windows 61.

The examiner then rotates the cross cylinder unit 128 to align the P mark 136 on the cross cylinder unit 128 with the astigmatic axis. When the astigmatic axis shown on the astigmatic axis conversion knob 122 and the astigmatic axis of the cross cylinder 130 are aligned, the controller 9 makes an informing display to that effect (such as by blinking the cross cylinder 130 or changing its color, for example). Based on an operation signal from the controller 9, the control part 202 controls the driving part 51 to dispose the cross cylinder in the optometry windows 61 in the designated rotation axis.

If the visibility is better when the red point 130R is at the P mark 136, the examiner turns the cylindrical power conversion knob 124 to increase the degree of astigmatism by a predetermined diopter power (such as 0.25 D). If the visibility is better when the white point 130W is at the P mark 136, the examiner turns the cylindrical power conversion knob 124 to decrease the degree of astigmatism by a predetermined diopter power (such as 0.25 D). The examiner repeats the operation until the visibility is substantially the same before and after the cross cylinder is inverted. When the visibility is the same, the degree of astigmatism is determined.

<Spherical Adjustment 2>

Next, the cross cylinder is removed, and the spherical diopter power on the most plus side where the maximum eyesight can be obtained by spherical adjustment (in the case of myopia, the minimum diopter power where the maximum eyesight can be obtained) is measured. Here, the examiner performs the above-described red-green test again, and ends the test in a state such that the red chart and the green chart are visible to the same degree, or a state such that the red chart is slightly more visible.

<Eyesight Confirmation>

An eyesight confirmation method will be described. The examiner, using the eyesight chart selection button 127, causes the target presenting unit 21 to display an eyesight table chart, and confirms the eyesight. For example, the examiner confirms the maximum eyesight by performing eyesight confirmation successively from the eyesight of around 1.0. While a maximum eyesight target is shown to the examinee, the spherical disc 120 is rotated to increase the spherical diopter power by +0.25 D. Based on an operation signal from the controller 9, the control part 202 controls the driving parts 50 to increase the spherical lens by 0.25 D. When a decrease in eyesight is confirmed, the operation is reversed. If there is no change, the spherical diopter power is further increased similarly by 0.25 D. When the maximum eyesight is confirmed, the process ends.

The examiner rotates the auxiliary lens knob 116 to set the right eye to occluder "OC" and the left eye to open "O" while looking at the auxiliary lens scale, and then performs the examination on the left eye in the same way as described above.

<Binocular Balance Test>

A binocular balance test method will be described. First, the target chart button 126 on the touchscreen display panel 30 is touched to display the target chart selection button 127. Among the displayed charts, a binocular balance chart is touched. The control part 206, based on an operation signal from the controller 9, presents a left-right binocular balance chart to the examinee's eye.

The examiner rotates the left-right auxiliary lens knob 116 to be aligned with the "P" polarizing plate. Based on an operation signal from the controller 9, the control part 206 controls the driving parts 50 to rotate the lens discs 64 so that a polarzing plate is set in each of the left and right optometry windows 61.

To the examinee, an upper letter will be visible with the right eye, and a lower letter will be visible with the left eye. The examinee is asked to confirm, and if there is a difference in visibility, the spherical disc 120 on the better visibility side is turned to increase the spherical diopter power by 0.25 D. Based on an operation signal from the controller 9, the control part 206 controls the driving parts 50 to modify the lenses disposed in the left and right optometry windows 61.

<Stereoscopic Vision Test>

A stereoscopic vision test method will be described. First, the examiner touches the target chart button 126 on the touchscreen display panel 30 to display the target chart selection button 127. Then, from among the displayed charts, the stereoscopic vision chart is touched. Based on an operation signal from the controller 9, the control part 206 presents a left-right stereoscopic vision chart to the examinee's eye.

The examiner rotates the left-right auxiliary lens knob 116 to be aligned with a "P" polaroid (polarizing plate). Based on an operation signal from the controller 9, the control part 206 controls the driving parts 50 to rotate the lens discs 64 so that the polarizing plate is set in each of the left and right optometry windows 61. In this state, it is confirmed to see if a stereoscopic vision is obtained by the examinee.

<Near Measurement>

A near measurement method will be described. First, the examiner touches the near/far switching button 137. Based on an operation signal from the controller 9, the control part 206 controls the driving part 53 to adjust the convergence angle of the left and right lens chamber units.

The examiner then causes the rod 2 set on a near-point rod holder (not illustrated) of the device main body 1 to fall forward. The near target presenting unit 4 is caused to display a cross grid. If the examinee is older than 50 or so, the spherical diopter power is increased by plus 1.00 D in advance.

Thus, the examiner rotates the spherical disc 120 to cause the spherical diopter power display portion 120a and the near target presenting unit to display the desired spherical diopter power. Based on an operation signal from the controller 9, the control part 206 controls the driving parts 50 to dispose the spherical lens having the displayed numerical value in the optometry windows 61. Then, the position of a near-point card 42 of the device main body 1 is aligned for the near distance.

The examiner rotates the auxiliary lens knob 116 to align the dial with the cross cylinder of ±0.50 with respect to the both eyes. Based on an operation signal from the controller 9, the control part 206 controls the driving parts 50 to dispose the cross cylinder lens in the left and right optometry windows. The examiner turns the spherical disc 120 to increase in +0.25 D steps until the vertical line and the lateral line of the cross grid have the same density.

In the foregoing description, the optometry apparatus main body 1 is configured to be operated by a rotating operation with respect to the rotating operating units on the display panel 30. However, this is not a limitation. The optometry apparatus main body 1 may be configured to be operated by a linear operation (such as a flip operation in a linear direction) with respect to the rotating operating units on the display panel 30. When the discs or various knobs on the display panel 30 are touched, the control part 204 causes a plurality of numerical values to be displayed in the vicinity of the touched operating unit. The optical element disposed in the optometry windows 61 is selected by touching the numerical values. In the case where the plurality of numerical values is displayed in the vicinity of the touched operating unit, numerical values displayed in a numerical sequence may be continuously switched when the finger is slid while touching a numerical value.

In the foregoing description, when the distance of the left and right optometry windows is adjusted, the PD adjusting knob 105 of the display panel 30 is rotated. However, this is not a limitation. The distance may be directly adjustable by sliding fingers to the left or right while touching the left and right lens chamber units 100*a*.

The method of displaying various numerical values may be freely set for analog display, digital display, or other display methods, and is not limited to any one method.

In the case of one-eye examination, the graphic image of the lens chamber unit 103 on the examined side may be enlarged when displayed on the display panel 30 in order to display greater details.

With reference to FIG. 12, a modification of the controller 9 will be described. A controller 9A illustrated in FIG. 12 is provided with a touchscreen display panel 30A. In the display panel 30A, a graphic image 100A of the manual optometry apparatus is displayed. The graphic image 100A is provided with convergence levers 115A. The examiner can touch the convergence levers 115A and slide inward, whereby the driving part 53 is driven and the convergence angle of lens chamber units 103A can be adjusted. Specifically, the controller 9 reads the direction and amount of operation with respect to the convergence levers 115A, and transmits a drive signal to the control part 202. The control part 202 controls the driving part 53 to adjust the convergence angle of the lens chamber units 100*a*.

With reference to FIG. 13, another modification of the controller 9 will be described. A controller 9B illustrated in FIG. 13 is provided with a touchscreen display panel 30B. In the display panel 30B, a graphic image 100B of the manual optometry apparatus is displayed. The controller 9B is also provided with dials 150B on the left and right ends. The dials 150B depict spherical discs of the manual optometry apparatus. The lens discs 64 of the device main body 1 can be controlled by rotating the dials 150B in the same way that the spherical discs 120 of the graphic image 100 are rotated. When the controller 9B of such configuration is used, the same action as in the above-described case of the controller 9 can be also performed. Further, by using the dials 140B, the lens discs can be controlled with the same feeling as if operating the manual optometry apparatus.

With reference to FIG. 14, yet another modification of the controller 9 will be described. A controller 9C illustrated in FIG. 14 is provided with a touchscreen display panel 30C. In the display panel 30C, a graphic image 100C of the manual optometry apparatus is displayed. In the controller 9C, the rotating operating unit to be operated next is displayed with emphasis relative to the other rotating operating units, in accordance with the procedure of an optometry program in which a subjective refractive power examination procedure for the examinee's eye is set in advance. The optometry program is stored in the memory 210, for example.

Namely, the controller 9C is provided with the function of letting the examiner know what to operate next by displaying with emphasis the operating unit which needs to be or can be operated for examination. In the example of FIG. 14, the cylindrical power conversion knob 124C is displayed with emphasis by enlargement and color inversion. The corresponding portion of the information display portion 125C is also displayed with color inversion for easier recognition. In this way, operation procedure guidance can be provided, whereby even an inexperienced examiner can perform the examination easily.

With reference to FIG. 15, yet another modification of the controller 9 will be described. A controller 9D illustrated in FIG. 15 is provided with a touchscreen display panel 30D and a screen direction detection unit, which is not illustrated. In the display panel 30D, a graphic image 100D of the manual optometry apparatus is displayed. The controller 9D has the function of switching the screen display depending on whether the screen direction is laterally held or longitudinally held. For example, when the screen direction is laterally held, as illustrated in FIG. 15, the left and right lens chamber units are displayed. When the screen direction is longitudinally held, as illustrated in FIGS. 16(*a*) and (*b*), one of the left and right lens chamber units is enlarged, displaying more detailed information. When the right-side lens chamber unit image is being displayed, the finger may be slid to the right while touching the display panel 30D to display the image of the left-side lens chamber unit. When the left-side lens chamber unit image is being displayed, the finger may be slid to the left while touching the display panel 30D to display the image of the right-side lens chamber unit.

Another modification of the controller will be described. The controller according to the present modification is provided with a touchscreen display panel and a vibration device (vibrator) for vibrating the controller in accordance with an operation. On the display panel, a graphic image of the manual optometry apparatus is displayed. The controller of the present modification is provided with the function of letting the examiner know that a touchscreen operation on the graphic image is ongoing or has been performed by vibrating the vibration device during or after the operation.

For example, in the controller, the vibration device generates vibration indicating the switching of the optical element disposed in the optometry window each time the spherical discs or rotation knobs on the touchscreen are operated.

Another modification of the controller will be described. The controller according to the present modification is provided with a touchscreen display panel and a voice generator for generating voice in accordance with an operation. On the display panel, a graphic image of the manual optometry apparatus is displayed. In the controller according to the present modification, voice is generated during or after a touchscreen operation on the graphic image on the touchscreen, letting the examiner know that the operation is ongoing or has been performed.

For example, in the controller, the voice generator generates a switching sound indicating the switching of the optical element disposed in the optometry window each time the spherical discs or rotation knobs on the touchscreen are operated.

As described above, the informing unit indicating the switching of the optical element disposed in the optometry window is provided, thereby configuring the controller to provide an operation feel closer to that of a manual refractor.

In the foregoing description, the control part 204 may be configured such that, when one operating unit is identified from among the plurality of operating units on the graphic image 100, the operation of the optometry apparatus main body 1 based on the operation of another operating unit is prohibited until the operation with respect to the identified operating unit is completed (for example, until a drag operation is completed). For example, the control part 204 invalidates the operation signal from the other operating unit and does not transmit a drive signal based on the other operating unit to the optometry apparatus main body 1. In this way, the operation of the optometry apparatus main body 1 against the examiner's intension can be avoided.

In the foregoing description, the manual refractor is configured such that the graphic image as viewed from the operator side is displayed as the operation screen, and a control signal is output to the electric refractor based on the touch input with respect to the graphic image on the touchscreen. However, this is not a limitation.

It is preferable if only an ophthalmic apparatus provided with a manual operating unit is configured such that a graphic image as viewed from the operator side is displayed as an operation screen, and a control signal is output to the ophthalmic apparatus based on a touch input with respect to the graphic image on the touchscreen (for example, a target presenting device).

<Second Embodiment>

In the following, a second embodiment will be described. The second embodiment differs from the optometry apparatus of the first embodiment in the display screen of the controller. Thus, the operation method for operating the optometry apparatus using the controller is different. Because the elements other than the controller are similar to those of the first embodiment, similar elements will be designated with similar numerals and their description will be omitted.

FIG. 17 illustrates an example of the display screen of the display panel 30 according to the present embodiment. In the present embodiment, with regard to the layout of the graphic image 400, a trial frame 400a is displayed so as to offer a work feeling similar to that of trial frame examination. Trial frame lenses 400b are displayed to the left and right of the trial frame 400a. The trial frame lenses 400b correspond to handled optometry lenses attached to the trial frame 400a.

The layout of the trial frame 400a will be described. The trial frame 400a includes lens mount frames 400a1, astigmatic axis angle scales 400a2, and a bridge 400a3. The bridge 400a3 is displayed at the screen center, linking the left and right lens mount frames 400a1. The axial angle scales 400a2 are displayed around the lens mount frames 400a1. At the center of the bridge 400a3, a forehead rest lamp 400a4 is displayed.

The layout of the trial frame 400a is not limited to the above display mode. For example, any graphic may be formed that suggests the trial frame spectacles as long as the layout is such that at least the lens mount frames 400a1 and the astigmatic axis angle scales 400a2 are displayed. Such layout may also be configured such that the axial angle scale and the like are additionally displayed in accordance with the purpose of use.

The layout of the trial frame lenses 400b will be described. The trial frame lenses 400b include spherical lenses 400b1, cylindrical lenses 400b2, and auxiliary lenses 400b3. The trial frame lenses 400b are respectively displayed to the left and right of the trial frame 400a. The trial frame lenses 400b are displayed with the spherical lenses 400b1 located above, the cylindrical lenses 400b2 at the center, and the auxiliary lenses 400b3 at the bottom. The location and positional relationship of the lenses are merely an example and not a limitation. For example, the order of location of the spherical lenses 400b1, the cylindrical lenses 400b2, and the auxiliary lenses b3 may be reversed. The layout including the spherical lenses 400b1, the cylindrical lenses 400b2, and the auxiliary lenses 400b3 may not form a left-right pair. Instead, the layout may be such that one set of the spherical lens 400b1, the cylindrical lens 400b2, and the auxiliary lens 400b3 is displayed. The layout of the trial frame lenses 400b are not limited to the above display mode and may be set in accordance with the required purpose of examination. For example, the spherical diopter power of the examinee's eye can be measured as long as the layout is such that at least the spherical lenses 400b1 are displayed. Such layout may also be configured such that an axial angle scale or the like is additionally displayed in accordance with the purpose of use.

An information display portion 425 is displayed in a peripheral portion of the screen (such as below), and displays the optical characteristics (such as the lens diopter power and the prism value) of the optical element disposed in front of the examinee's eye in the optometry apparatus main body 1. A target chart selection button 427 is displayed in a peripheral portion of the screen (such as above) and used for selecting the target presented by the target presenting device 20.

PD (pupillary distance) adjust buttons 405 are displayed under the left and right lens frame mount frames 400a1, and used for adjusting the distance between the left and right lens mount frames 400a1. A PD display portion 407 is displayed over the trial frame 400a. In the PD display portion 407, the distance between the left and right optometry windows 61 is displayed. An adjusting near/far switching button 437 is displayed in the space between the PD adjusting buttons 405. The adjusting near/far switching button 437 is used for switching the convergence angle of the optometry windows 61 when switching between near measurement and far measurement.

Spherical diopter power plus buttons 441 and spherical diopter power minus buttons 442 are displayed in the vicinity of the left and right spherical lenses 400b1, and used for adding or subtracting the spherical diopter power of the optical element 65 disposed in the optometry windows 61 in predetermined steps (such as 0.25 D or 0.5 D). Cylindrical power plus buttons 443 and cylindrical power minus buttons 444 are displayed in the vicinity of the left and right cylindrical lenses 400b2 and used for adding or subtracting the cylindrical power of the optical element 65 disposed in the optometry windows 61 in predetermined steps (such as 0.25 D or 0.5 D). The layout of the various display portions or buttons is not limited to the above-described display mode, and may be set in accordance with the required examination purpose.

A method of operating the controller 9 using the graphic image 400 will be described. On the display panel 30, a signal for driving the driving parts 50 to 53 of the optometry apparatus main body 1 is input by the touch of the examiner's finger (or a stylus). In the graphic image 400, a plurality of operating members for driving the optometry apparatus main body 1 is formed. The spherical lenses 400b1, the cylindrical lenses 400b2, the auxiliary lenses 400b3, the PD adjusting buttons 405, the target chart selection buttons 427, the near/far switching button 437, the spherical diopter power plus buttons 441, the spherical diopter power minus buttons 442, the cylindrical power plus buttons 443, and the cylindrical power minus buttons 444 are respectively used as the operating member on the graphic image 400.

When at least one of the operating members on the graphic image 400X is touched or dragged by the examiner, a drive signal corresponding to the touched or dragged operating member is output to the optometry apparatus main body 1. The drive signal includes, e.g., drive information relating to the direction and amount of movement of at least one device element of the optometry apparatus main body 1. The optometry apparatus main body 1 causes the driving parts (50 to 53) to be driven in accordance with the signal from the controller 9.

Here, the control part 204 identifies one operating member from among the plurality of operating members displayed on the graphic image 400 in accordance with the coordinate position touched on the touchscreen. For example, the control part 204 transmits a drive signal to the optometry apparatus main body 1 based on the operation signal with respect to the identified operating member.

The drive signal is sent from the controller 9 to the control part 202 of the optometry apparatus main body 1 via the relay unit 12. The control part 202 identifies from among the plurality of driving parts 50 to 53 the driving part corresponding to the drive signal from the controller 9. The control part 202 controls the identified driving part with the direction and amount of driving corresponding to the operation on the controller 9.

The driving parts 50 and 51 of the optometry apparatus main body 1 may not necessarily be directly driven in accordance with the operation with respect to the graphic image 400 on the controller 9. For example, the control part 204 of the controller 9 may determine the optical element to be disposed in the optometry windows 61 of the lens chamber units 600 in accordance with the operation on the controller 9, and transmit a drive signal for disposing the determined optical element in the optometry windows 61 to the optometry apparatus main body 1. Based on the drive signal, the control part 202 of the optometry apparatus main body 1 controls the driving parts 50 and 51 to dispose the determined optical element in the optometry windows 61. A similar setting may be made for the driving of the driving parts 52 and 53 in accordance with an operation signal from the controller 9.

In the following, an operation corresponding to each operating member will be described. FIG. 18(a) illustrates the controller 9 prior to operating the PD adjusting button 405. When the PD adjusting button 405 is dragged in the direction of the arrow, the distance between the optometry windows becomes smaller, as illustrated in FIG. 18(b). FIGS. 19 to 21 illustrate the flow of the operation performed with respect to the controller when the examiner disposes a spherical lens of −5.00 D in the optometry window 61. FIGS. 22 to 24 illustrate the flow of operation performed with respect to the controller when the examiner disposes a cylindrical lens of −1.00 D in the optometry window 61 at the axial angle of 140°. FIGS. 25 to 26 illustrate the flow of operation performed with respect to the controller when the examiner disposes the cross cylinder in the optometry window 61 and then inverts the axis.

Referring mainly to FIG. 2, FIG. 3, and FIG. 17, specifically, when the PD adjusting button 405 is touched by the finger and operated to the left or right, the distance of the left-right lens mount frame 400a is adjusted. The controller 9 reads the direction and amount of operation with respect to the PD adjusting buttons 405, and transmits a drive signal to the control pan 202. The control part 202 controls the driving part 52 to adjust the distance between the left and right optometry windows 61. In the PD display portion 407 on the display panel 30, the distance between the left and right optometry windows 61 is displayed. When the distance between the left and right optometry windows 61 is modified, the PD display portion 407 displays information corresponding to the modified distance.

When a pressure is applied to the forehead rest 70 of the device main body 1, the pressure detection part 203 included in the forehead rest 70 detects the pressure and transmits a signal to the control part 202 of the optometry apparatus main body 1. An instruction signal from the control part 202 is sent to the control part 204 of the controller 9 via the control part 200 in the relay unit 12. The control part 204, based on a detection result from the pressure detection pan 203, controls the forehead rest lamp 400a4 on the graphic image 400. For example, when the forehead of the examinee is properly affixed onto the forehead rest 70, the lamp 400a4 is turned off. When the forehead of the examinee is not properly affixed onto the forehead rest 70, the lamp 400a4 is turned on. Obviously, the lamp 400a4 may be turned on when the forehead of the examinee is properly affixed onto the forehead rest 70, while the lamp 400a4 may be turned off when the forehead of the examinee is not properly affixed onto the forehead rest 70.

When the finger touches the spherical lens 400b1, a spherical diopter power selection screen 451 is displayed. In the spherical diopter power selection screen 451, a plurality of different spherical diopter powers is displayed in a list, for example, as illustrated in FIG. 19(b). The examiner selects the spherical diopter power by touching the spherical diopter powers displayed in the spherical diopter power selection screen 451. When the desired spherical diopter power is not displayed in the spherical diopter power selection screen 451, the desired spherical diopter power is caused to be displayed by touching the upper or lower triangular button or by dragging the spherical diopter power selection screen 451 up or down (see FIG. 20(a)). Then, the spherical diopter power is selected by touching (see FIG. 20(b)). The selected spherical diopter power is displayed as inverted. In this state, when a spherical diopter power determination button 453 on the spherical diopter power selection screen 451 is touched, the spherical diopter power display screen 451 ceases to be displayed, and the selected spherical diopter power is displayed on the spherical lens 400b1. This time, when the spherical lens 400b1 is dragged to the vicinity of the lens mount frames 400a1, the spherical lens 400b1 being dragged is set in the lens mount frame 400a1. Further, the display of the S value (spherical diopter power value) in the information display portion 425 is switched to the selected spherical diopter power (see FIG. 21). The controller 9 reads the operation information with respect to the spherical lens 400b1 and the lens mount frame 400a1, and transmits a drive signal to the control part 202. The control part 202 then controls the driving part 50 to dispose the spherical lens corresponding to the display in the information display portion 425 in the optometry window 61.

When the finger touches the cylindrical lens 400b2, a cylindrical power selection screen 455 is displayed. The examiner selects a cylindrical power by touching the cylindrical power displayed in the cylindrical power selection screen 455. In the cylindrical power selection screen 455, a plurality of different cylindrical powers is displayed in a list, for example, as illustrated in FIG. 22. When the desired cylindrical power is not displayed in the cylindrical power selection screen 455, the desired cylindrical power is caused to be displayed by touching the upper or lower triangular button or by dragging the cylindrical power selection screen 455 up or down. Then, the cylindrical power is touched to select. The selected cylindrical power is displayed as inverted (see FIG. 22(b)). In this state, when a spherical diopter power determination button 457 on the cylindrical power selection screen 455 is touched, the cylindrical power display screen 455 ceases to be displayed, and the selected cylindrical power is displayed on the cylindrical lens 400b2 (see FIG. 23(a)). Now, when the cylindrical lens 400b2 is dragged to the vicinity of the lens mount frame 400a1 (see FIG. 23(b)), the cylindrical lens 400b2 being dragged is set in the lens mount frame 400a1. Further, the display of the C value (cylindrical power value) in the information display portion 425 is switched to the selected cylindrical power (see FIG. 24(a)). The controller 9 reads the operation information with respect to the cylindrical lens 400b2 and the lens mount frame 400a1, and transmits a drive signal to the control part 202. The control part 202 controls the driving parts 50 to dispose the cylindrical lens corresponding to the display in the information display portion 425 in the optometry window 61.

When a handle 400c2 of the cylindrical lens 400b2 set in the trial frame 400a is touched by the finger and the cylindrical lens 400b2 is rotated in the circumference direction thereof, the cylindrical lens 400b2 is rotated in the operated direction and relative to the astigmatic axis angle scale 400a2 (see FIG. 24(b)). The cylindrical lens 400b2 is rotated about the rotation axis at the center of the lens mount frames 400a1, for example.

On the cylindrical lens 400b2, astigmatic axis marks 400d2 are formed. The display of the astigmatic axis marks 400d2 is rotated in operative association with the rotation of the cylindrical lens 400*b*2 in the circumference direction. The examiner can easily confirm the astigmatic axis angle based on the position relationship between the astigmatic axis marks 400*d*2 and the astigmatic axis angle scale 400*a*2. In the above operation, the cylindrical lens 400*b* may be rotated in the circumference direction of the cylindrical lens 400*b*2 when the finger touches the main body of the cylindrical lens 400*b*2.

The examiner, referring to the astigmatic axis angle scale 400*a*2 attached to the lens mount frame 400*a*1 and the information display portion 425, makes an adjustment to the desired astigmatic axis angle. The controller 9 reads the direction and amount of operation with respect to the cylindrical lens 400*b*2, and transmits a drive signal to the control part 202. The control part 202 controls the driving part 51 to adjust the astigmatic axis of the cylindrical lens disposed in the optometry window 61.

When the finger touches the auxiliary lens 400*b*3 (see FIG. 25(*a*)), an auxiliary lens selection screen 459 is displayed (see FIG. 25(*b*)). In the auxiliary lens selection screen 459, a plurality of optometry auxiliary optical members is displayed in a list, for example, as illustrated in FIG. 25(*b*). The examiner selects an auxiliary lens by touching an auxiliary lens name displayed in the auxiliary lens selection screen 459. Upon selection, the auxiliary lens name is displayed as inverted. In this state, when an auxiliary lens determination button 161 on the auxiliary lens selection screen 459 is touched, the auxiliary lens display screen 459 ceases to be displayed, the type of the auxiliary lens 400*b*3 is switched, and the selected auxiliary lens name is displayed on the auxiliary lens 400*b*3 (see FIG. 26(*a*)). Then, when the auxiliary lens 400*b*3 is dragged to the vicinity of the lens mount frame 400*a*1, the auxiliary lens 400*b*3 being dragged is set in the lens mount frame 400*a*1. The controller 9 reads the operation information with respect to the auxiliary lens 400*b*3 and the lens mount frame 400*a*1, and transmits a drive signal to the control part 202. The control part 202 then controls the driving parts 50 to dispose the auxiliary lens corresponding to the auxiliary lens 400*b*3 set in the lens mount frame 400*a*1 in the optometry window 61.

When the trial frame lens 400*b* is removed from the optometry window 61, the trial frame lens 400*b* set in the lens mount frame 400*a*1 is dragged away from the lens mount frame 400*a*1 by touching the handle. In this way, the trial frame lens 400*b* can be returned to the predetermined position. The controller 9 reads the operation information with respect to the trial frame lens 400*b* and the lens mount frame 400*a*1, and transmits a drive signal to the control part 202. The control part 202 controls the driving parts 50 to remove from the optometry window 61 the optical element corresponding to the trial frame lens 400*b* removed from the lens mount frame 400*a*1. The method of removing the lens is not limited to the operation with respect to the trial frame lens 400*b*. For example, the corresponding lens may be removed by having a lens removing button displayed in the vicinity of each trial frame lens 400*b* and then operating the button.

When the examiner wishes to switch the presented target, the examiner touches, from among the target chart selection buttons 427, a chart button for the desired target formed on the screen (see FIG. 17). When the target chart selection button 427 is touched, the control pan 204 detects which switch has been touched.

In the target chart selection buttons 427, a plurality of various targets is displayed. When the desired target is touched by the finger, the target is selected. The selected target is selectively displayed on the display panel 30 (for example, the display color is inverted). The controller 9 transmits a control signal for presenting the selected target to the examinee to the control part 206. The control part 206 controls the target presenting unit 21 to present the selected target to the examinee.

In the configuration of the second embodiment described above, the examiner can operate the electric optometry apparatus by handling the controller with an operation feeling similar to that for trial frame examination. Thus, an examiner who is used to the trial frame spectacles and not to the electric optometry apparatus can easily operate the electric optometry apparatus.

Accordingly, the examiner who has been using the manual optometry apparatus including the trial frame spectacles and a trial lens set can be encouraged to introduce the electric refractor.

In the foregoing description, the operation screen including the trial frame 400*a* and the trial frame lenses 400*b* has been described by way of example. However, this is not a limitation. The controller 9 may include a touchscreen configured to display an operation screen for operating the optometry apparatus main body 1 and an operating unit for selecting the trial lens disposed in front of the examine's eye, and the controller 9 may display, as an operation screen, a target display (such as the trial frame 400*a*) set for switching the optical element and a graphic image (see the trial frame lenses 400*b*, for example) indicating the trial lens. Then, based on a graphic image moving operation toward where the target display is formed, the controller 9 outputs, to the optometry apparatus main body 1, a control signal for disposing the optical element corresponding to the trial lens, which is selected in advance by the operating unit, at the examinee's eye. Namely, the target display is not limited to the trial frame 400*a* and may have any display mode that provides a target for disposing the optical element corresponding to the trial lens selected in advance at the examinee's eye. For example, a frame display of a predetermined shape (such as a round frame, a rectangle, star-shape and the like) or an area display with a different color from the other portions may be considered.

The controller 9 also includes a touchscreen configured to display an operation screen for operating the optometry apparatus main body 1, and an operating unit for selecting the trial lens disposed in front of the examinee's eye, and displays a target display (such as the trial frame 400*a*) set for switching the optical element, a graphic image (such as the spherical lenses 400*b*1, and the spherical diopter power selection screen 451) for selecting the spherical diopter power, a graphic image (such as the cylindrical lenses 400*b*2 and the cylindrical power selection screen 455) for selecting the cylindrical power, and a graphic image (such as the auxiliary lenses 400*b*3 and the auxiliary lens selection screen 459) for selecting the auxiliary lens.

The graphic images for selecting the spherical diopter power, the cylindrical power, and the auxiliary lens are not limited to lens-shaped graphics, and may include a display mode such that the spherical diopter power, the cylindrical power, and the auxiliary lens can be distinguished, and such that a selection screen is displayed for each graphic of the spherical diopter power, the cylindrical power, and the auxiliary lens. For example, a frame display of a predetermined shape (such as a round frame, a rectangle, or star-shape), or an area display with a different color from the other portions may be considered.

BRIEF DESCRIPTION OF THE DRAWINGS

FIG. 8 illustrates the operation of a turret displayed on the controller.

FIG. 9 illustrates the operation of an auxiliary lens knob displayed on the controller.

FIG. 10 illustrates the operation of a spherical disc displayed on the controller.

FIG. 11 illustrates the operation of a cylindrical power conversion knob displayed on the controller.

FIG. 18 illustrates the operation of a PD adjusting button displayed on the controller.

FIG. 19 illustrates an operation procedure for modifying the spherical diopter power using the controller.

FIG. 20 illustrates an operation procedure for modifying the spherical diopter power using the controller.

FIG. 21 illustrates an operation procedure for modifying the spherical diopter power using the controller.

FIG. 22 illustrates an operation procedure for modifying the cylindrical power and the astigmatic axis angle using the controller.

FIG. 23 illustrates an operation procedure for modifying the cylindrical power and the astigmatic axis angle using the controller.

FIG. 24 illustrates an operation procedure for modifying the cylindrical power and the astigmatic axis angle using the controller.

FIG. 25 illustrates an operation procedure for inverting the cross cylinder using the controller.

FIG. 26 illustrates an operation procedure for inverting the cross cylinder using the controller.

DESCRIPTION OF REFERENCE SIGNS

Figure 1:
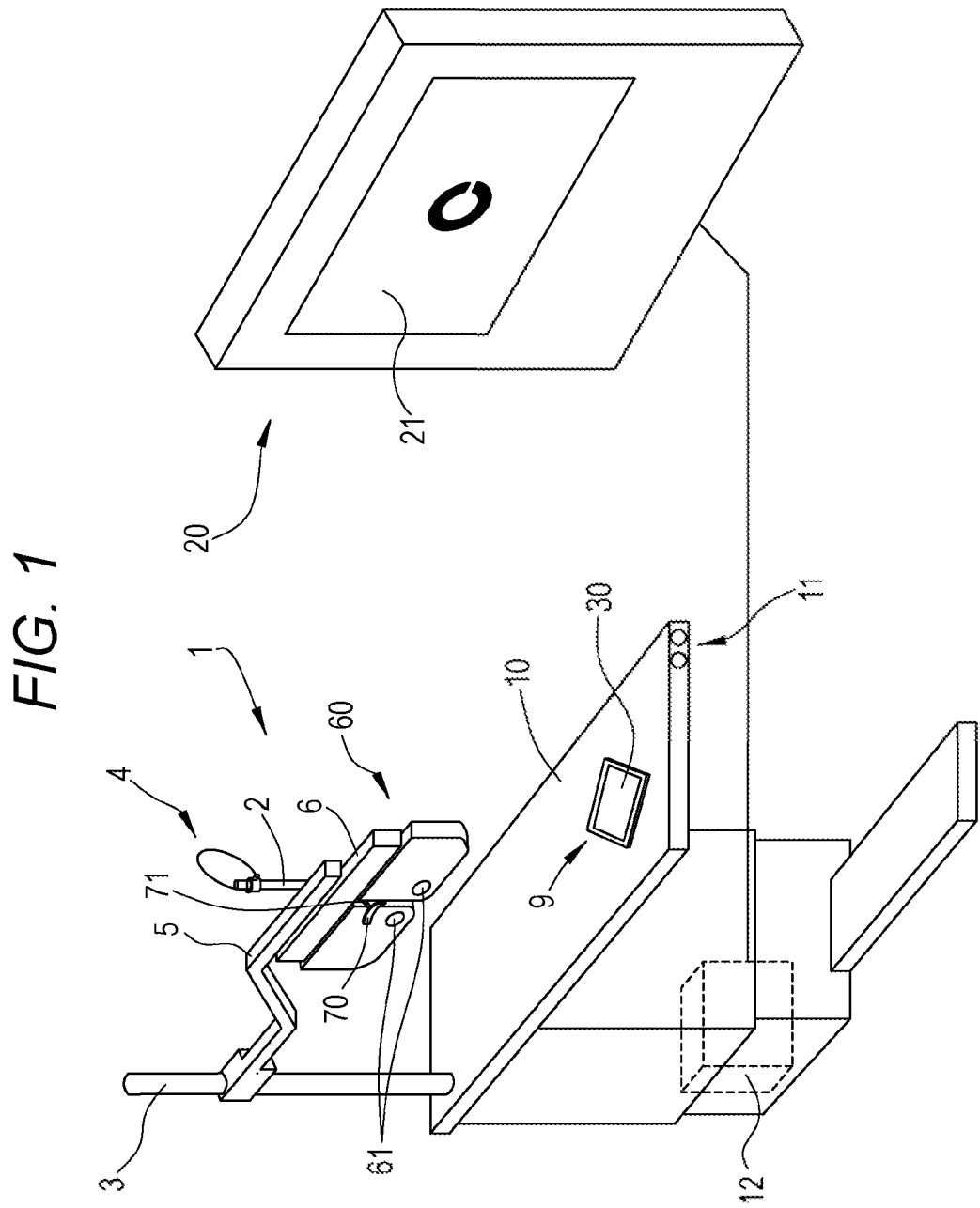
FIG. 1 is a schematic diagram of an optometry system as a whole according to the present embodiment.
Figure 2:
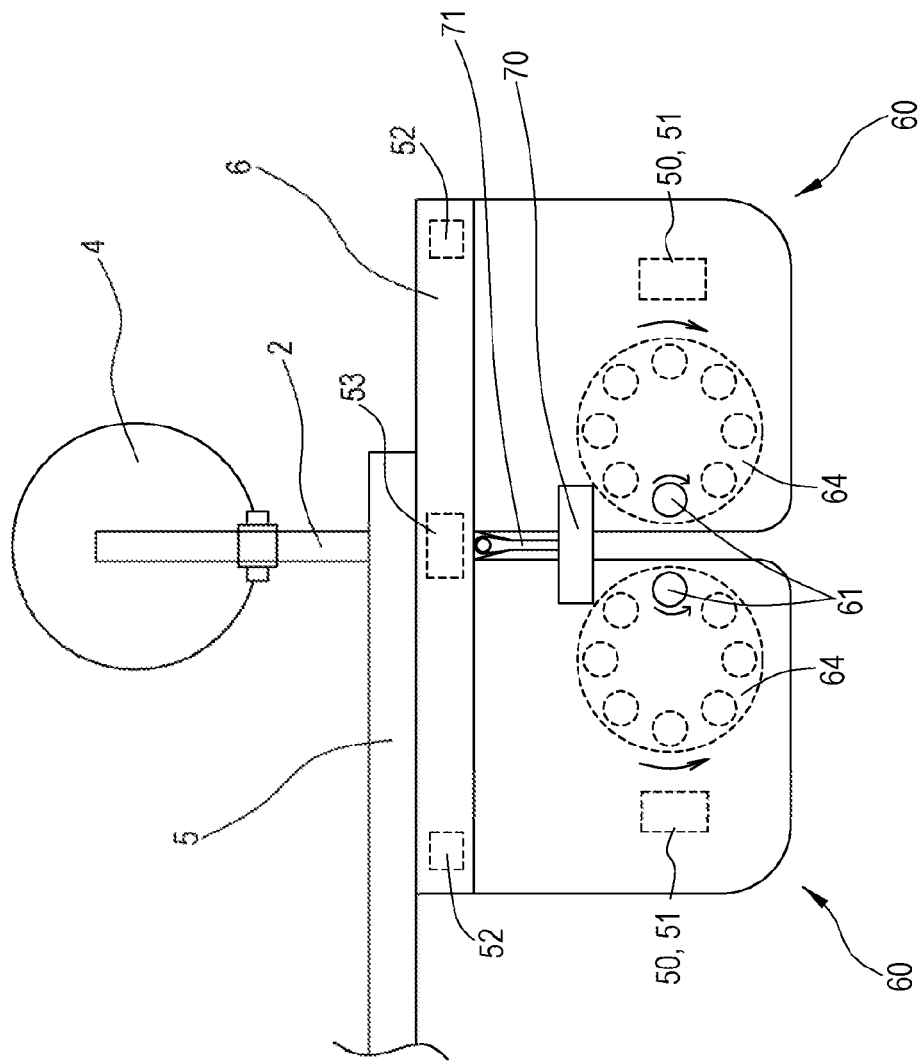
FIG. 2 is a schematic exterior diagram of an optometry apparatus according to the present embodiment as viewed from the examinee side.
Figure 3:
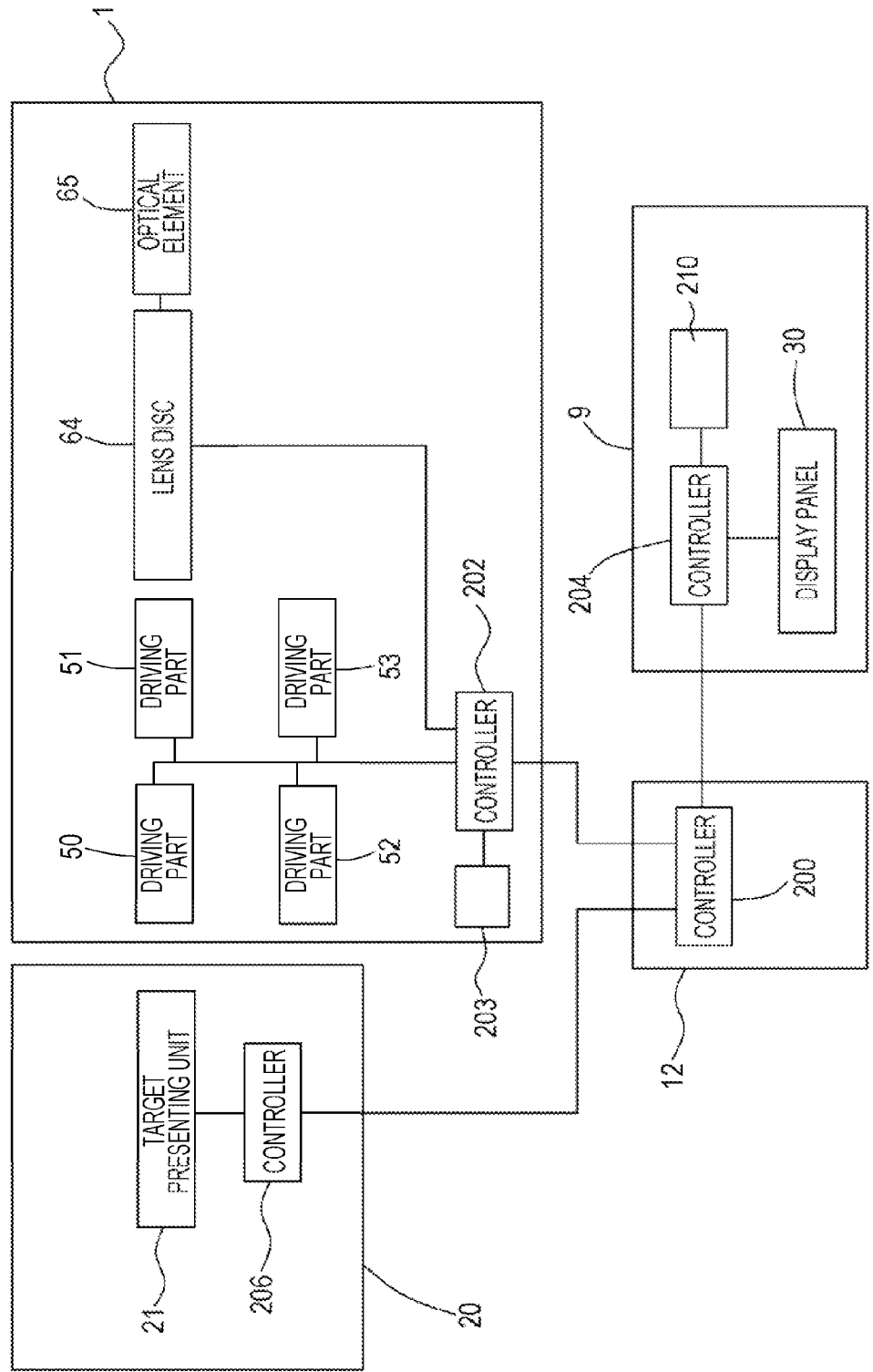
FIG. 3 is a control system block diagram according to the present embodiment.
Figure 4:
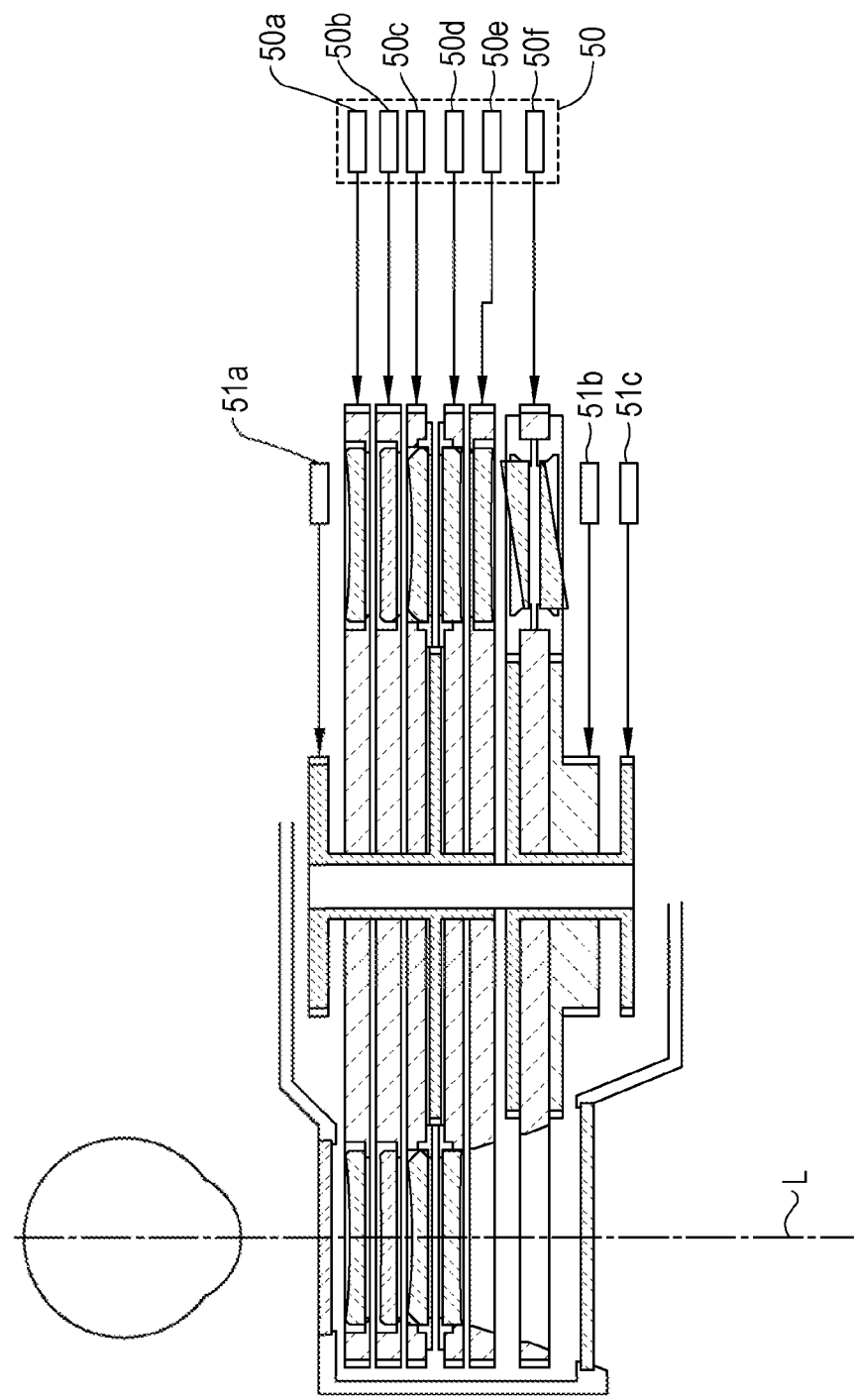
FIG. 4 illustrates an example of lens discs according to the present embodiment.
Figure 5:
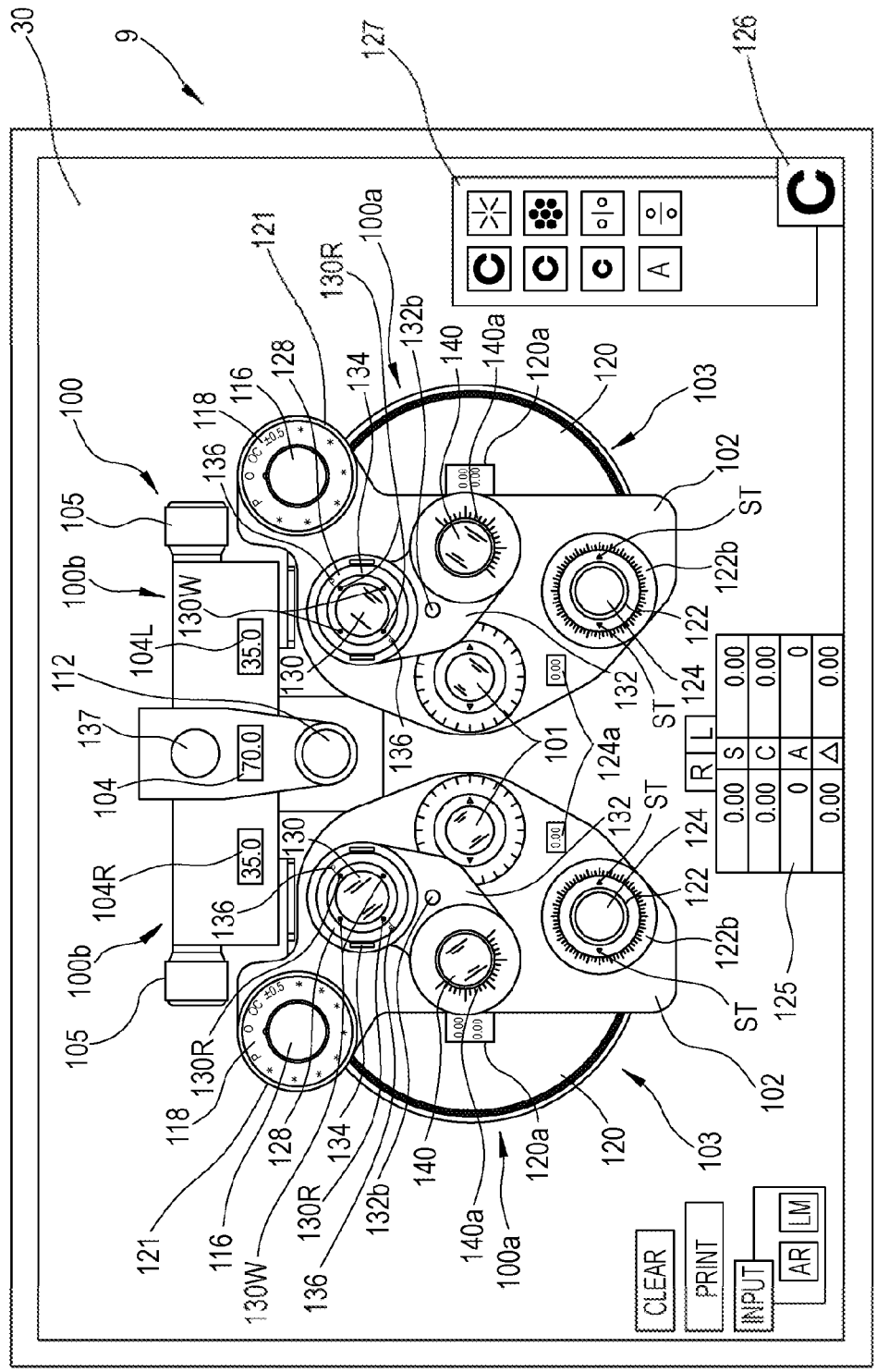
FIG. 5 is a schematic diagram of a controller according to the present embodiment.
Figure 6:
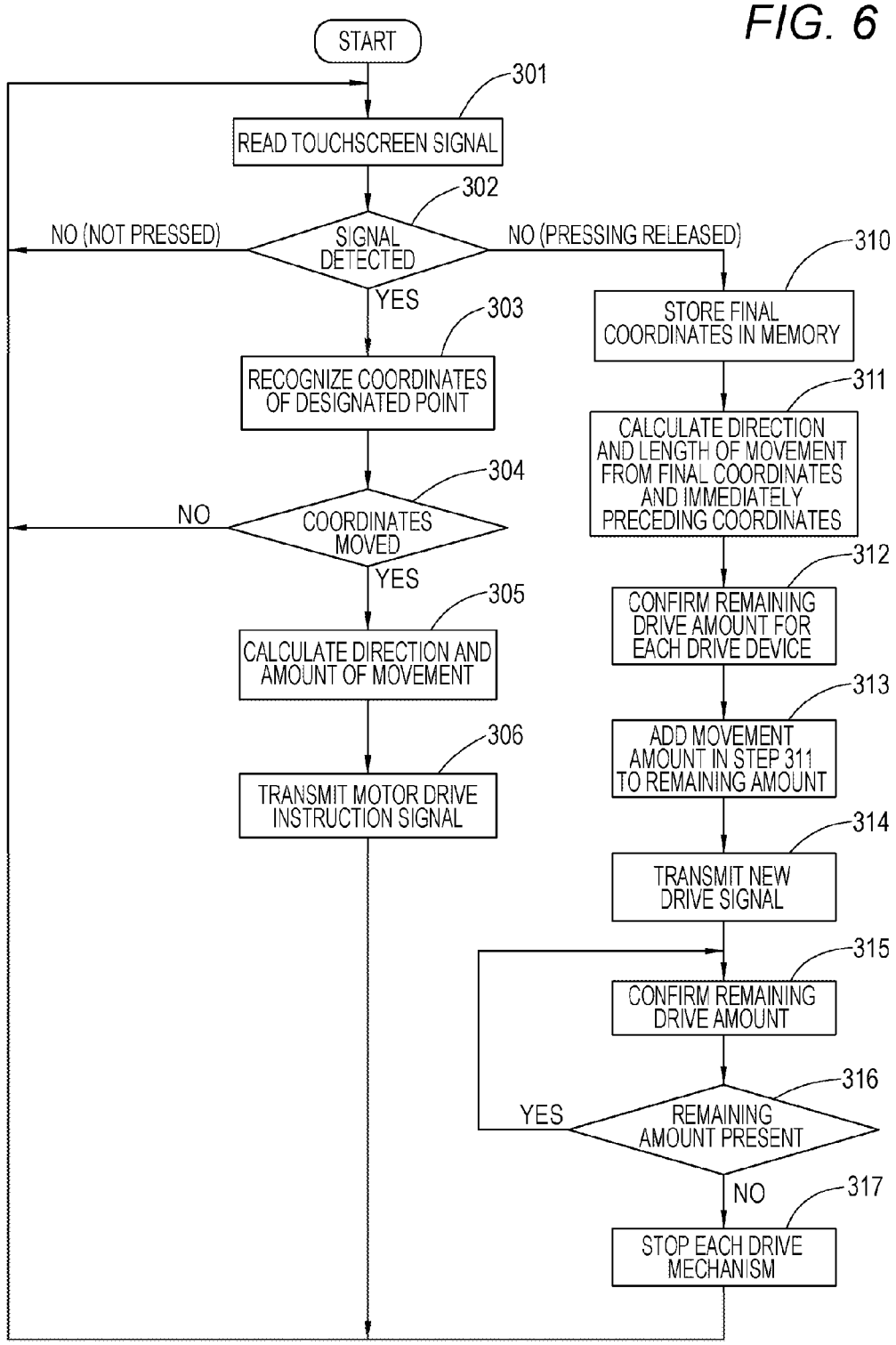
FIG. 6 is a flowchart describing the control for driving driving parts of a lens chamber unit by the dragging of a point designated on a touchscreen.
Figure 7:
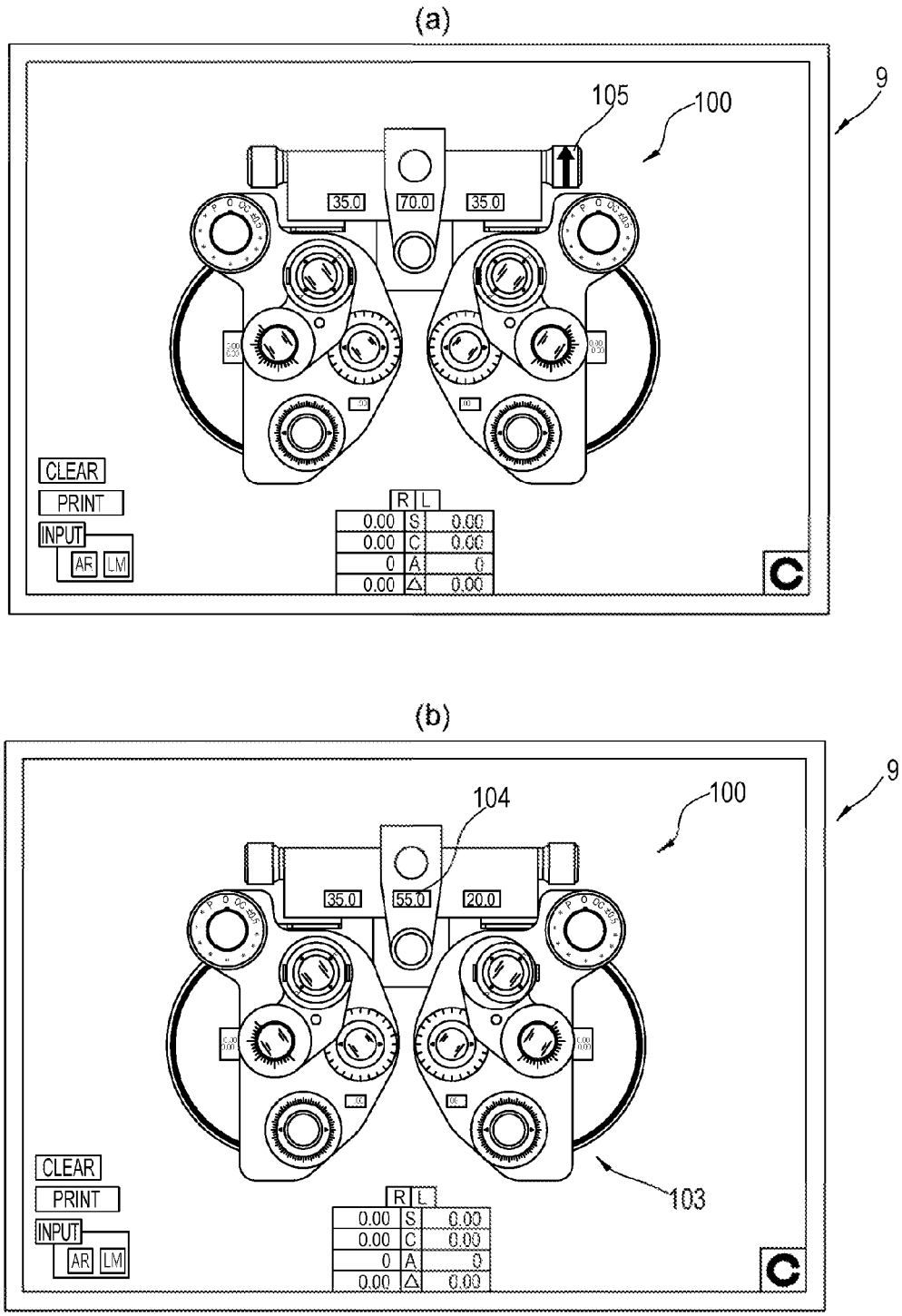
FIG. 7 illustrates the operation of a PD adjusting knob displayed on the controller.
Figure 12:
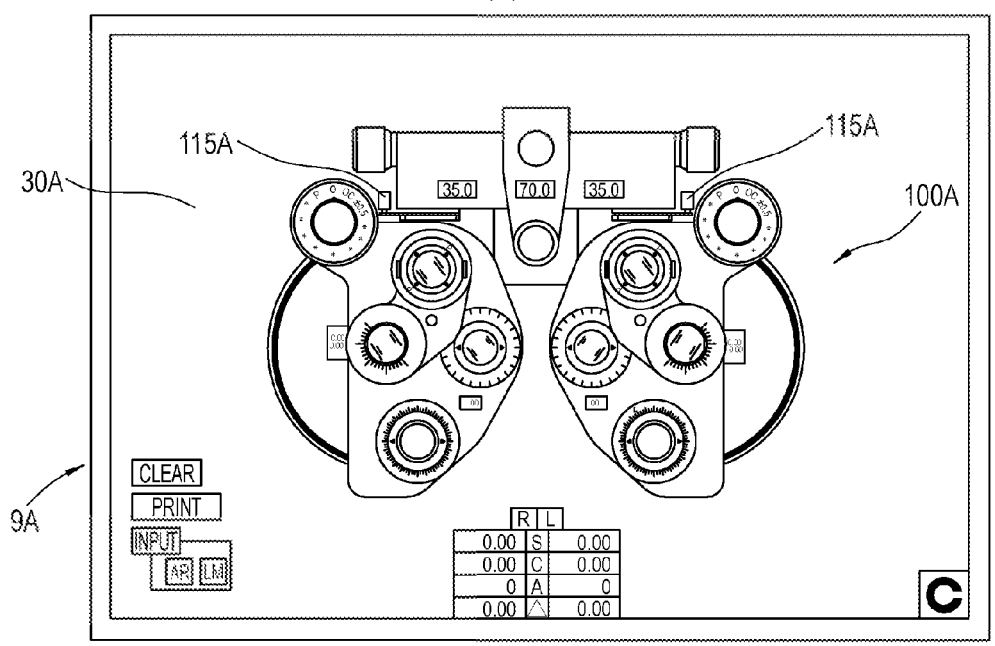
FIG. 12 illustrates a modification of the controller.
Figure 13:
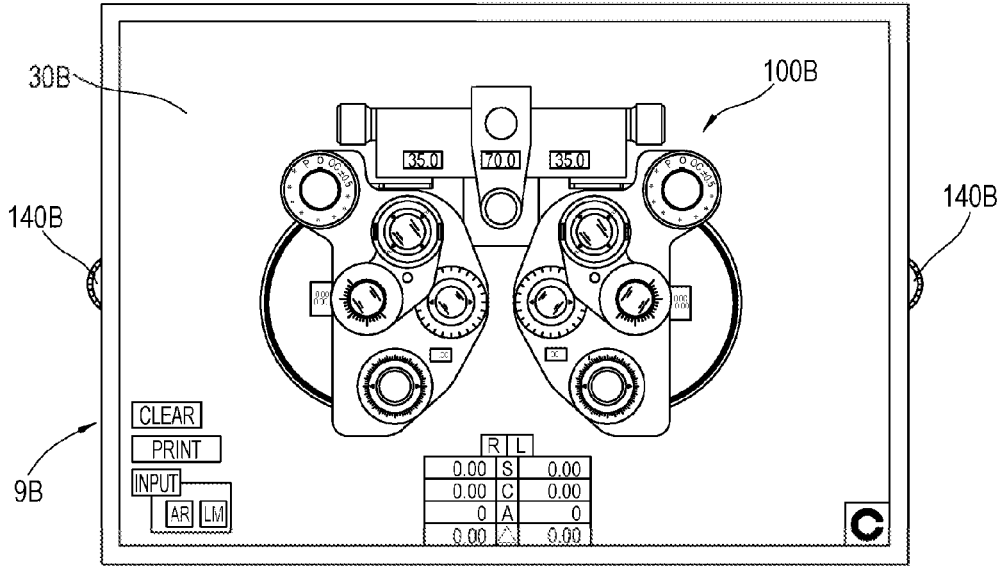
FIG. 13 illustrates a modification of the controller.
Figure 14:
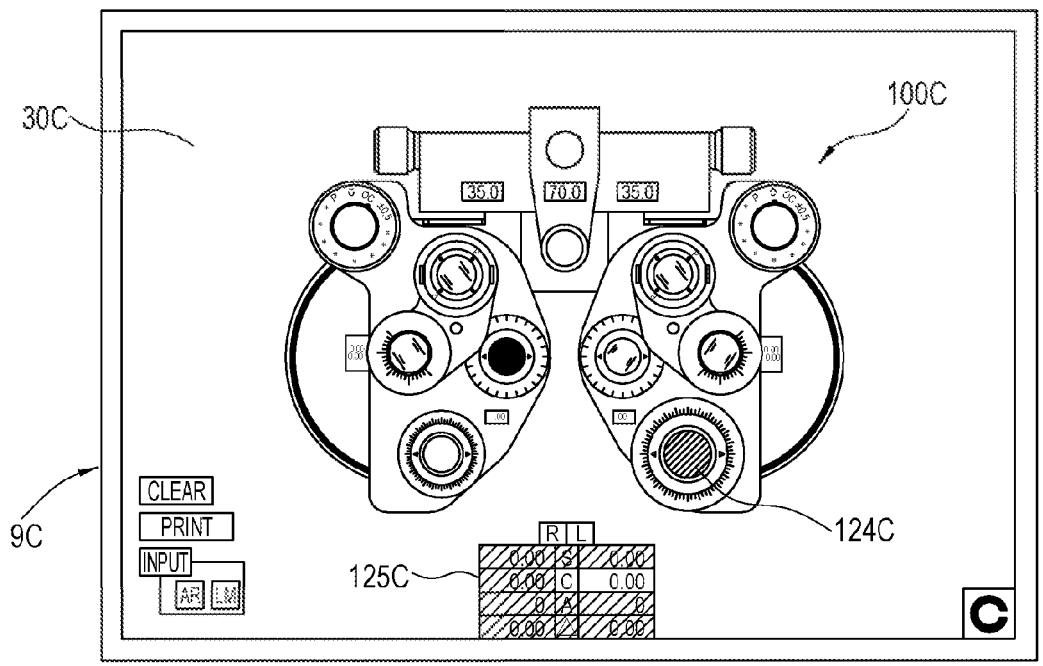
FIG. 14 illustrates a modification of the controller.
Figure 15:
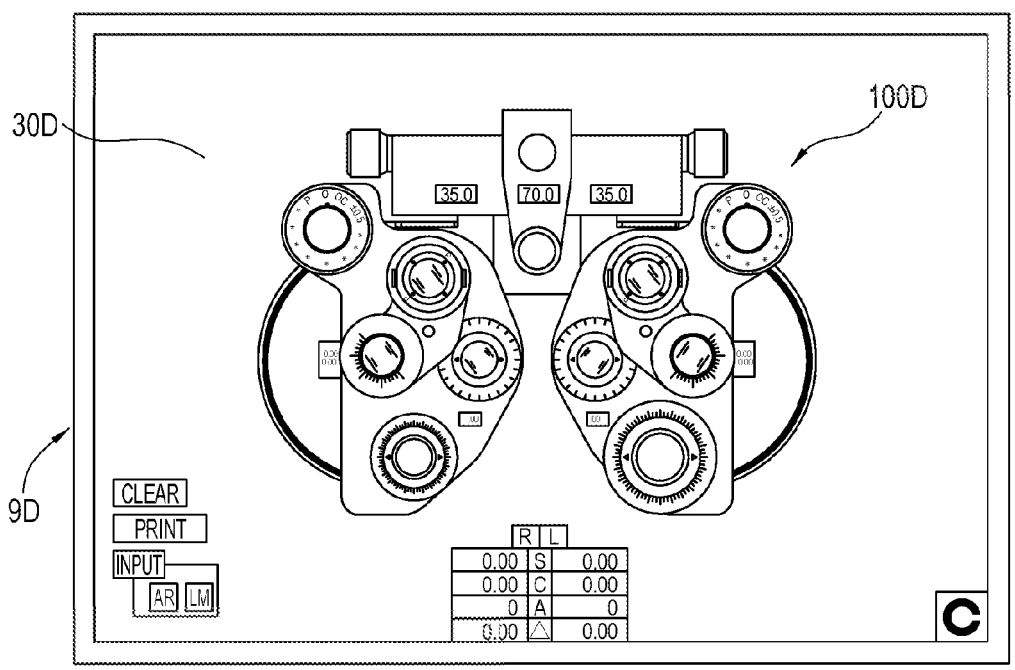
FIG. 15 illustrates a modification of the controller.
Figure 16:
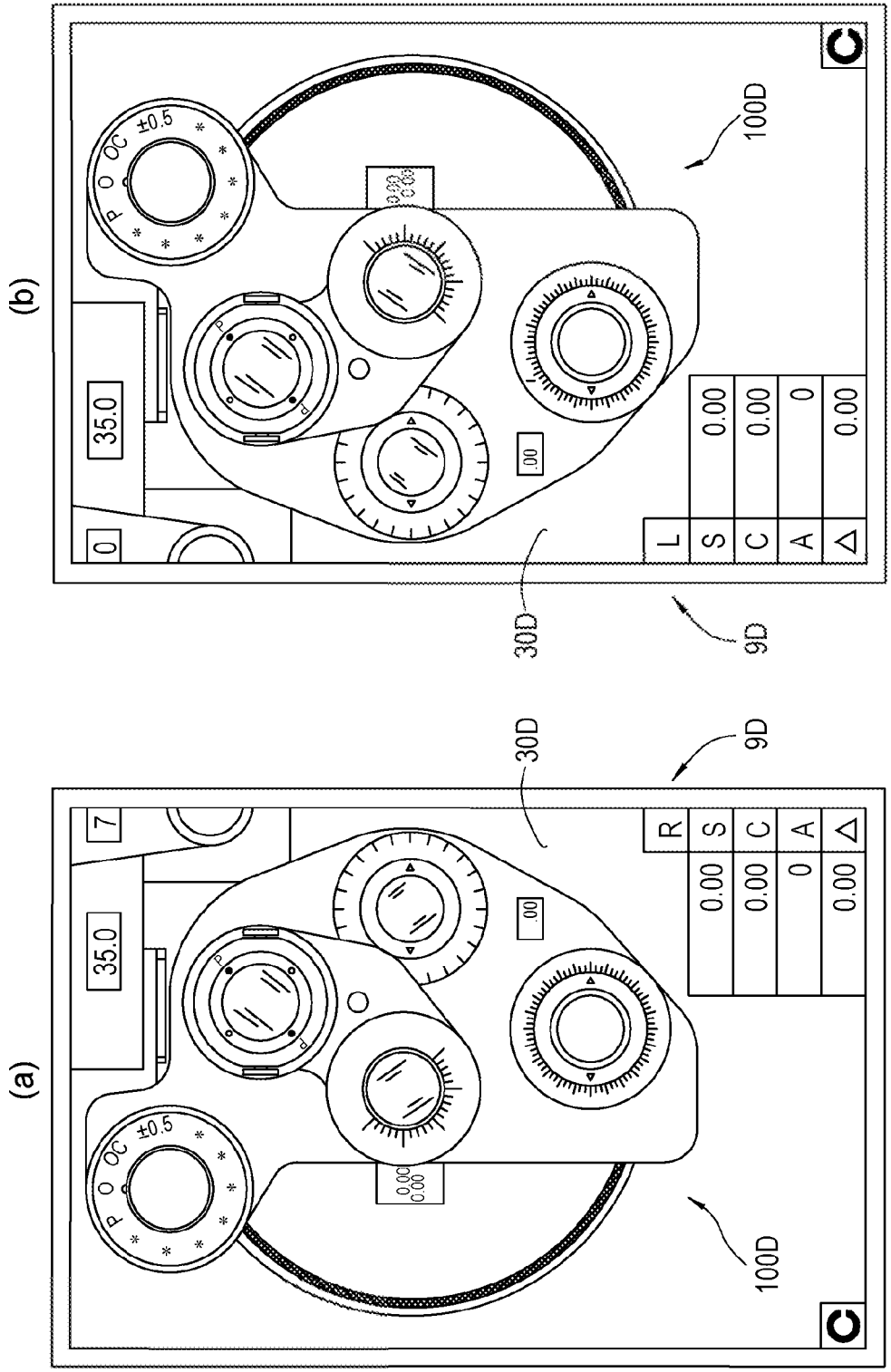
FIG. 16 illustrates a modification of the controller.
Figure 17:
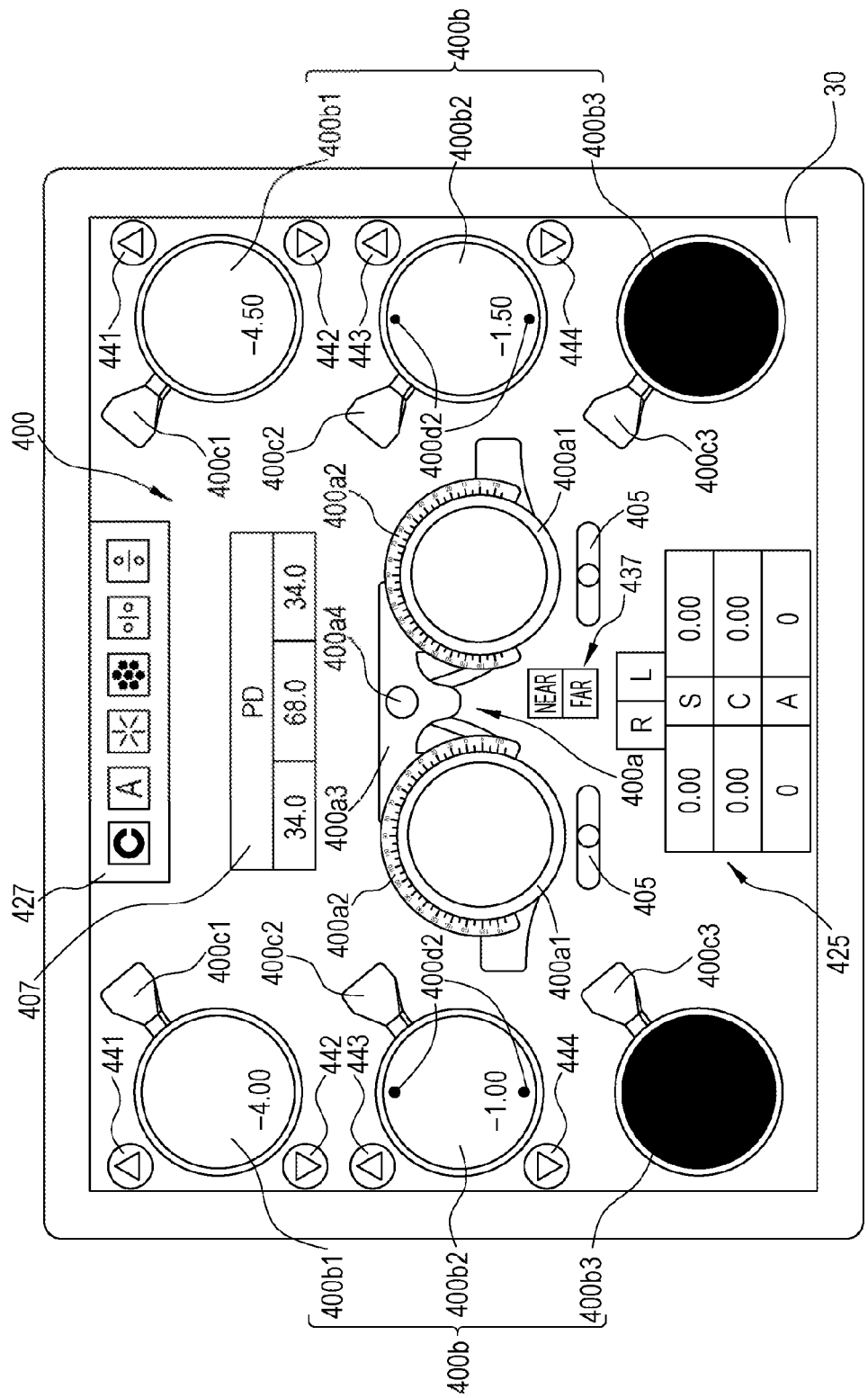
FIG. 17 is a schematic diagram of the controller according to the second embodiment.

1 Apparatus main body
6 Movable unit
9 Controller
12 Relay unit
20 Target presenting device
30 Display panel
60 Lens chamber units
61 Optometry window
64 Lens disc
65 Optical element
101 Optometry window
102 Lens chamber unit main body
105 PD adjusting knob
112 Forehead rest lamp
116 Auxiliary lens knob
120 Spherical disc
122 Astigmatic axis conversion knob
124 Cylindrical power conversion knob
125 Cylindrical power display portion
126 Target chart button
130 Cross cylinder
134 Cross cylinder knob
137 Near/far switching button
400a Trial frame
400a1 Lens mount frame
400a2 Astigmatic axis angle scale
400a3 Bridge
400a4 Forehead rest lamp
400b Trial frame lens
400b1 Spherical lens
400b2 Cylindrical lens
400b3 Auxiliary lens
405 PD adjusting button
407 PD display portion
425 Information display portion
427 Target chart selection button
437 Near/far switching button
441 Spherical diopter power plus button
442 Spherical diopter power minus button
443 Cylindrical power plus button
444 Cylindrical power minus button
451 Spherical diopter power selection screen
453 Spherical diopter power determination button
455 Cylindrical power selection screen
457 Cylindrical power determination button
459 Auxiliary lens selection screen
461 Auxiliary lens determination button

The invention claimed is:

1. An optometry apparatus controller provided in an electric optometry apparatus main body including an optical element disposed in front of an examinee's eye and a switch mechanism that electrically switches the optical element, for instructing the switching of the optical element, wherein
the controller
includes a touchscreen configured to display an operation screen for operating the electric optometry apparatus main body,
displays, as the operation screen, a graphic image of a manual optometry apparatus as viewed from an operator side, the manual optometry apparatus including a plurality of operating units and being configured to switch the optical element disposed in front of the eye by an operation with respect to the operating units, and
outputs a control signal to the electric optometry apparatus main body based on a touch input with respect to the graphic image on the touchscreen, and
the electric optometry apparatus main body switches a plurality of diopter powers of the optical element included in the electric optometry apparatus main body based on the touch input with respect to the graphic image on the touchscreen.

2. The optometry apparatus controller according to claim 1, wherein:
the controller displays, as the operation screen, the graphic image of a manual refractor as viewed from the operator side, the manual refractor including a lens chamber unit and a plurality of rotating operating units provided in the lens chamber unit, and being configured to mechanically switch the optical element disposed in front of the eye by a rotating operation with respect to the plurality of rotating operating units; and the controller outputs the control signal to the optometry apparatus main body based on the touch input with respect to the graphic image on the touchscreen.

3. The optometry apparatus controller according to claim 2, wherein the controller, in the operation screen, displays, as the operation screen, the graphic image in which at least the lens chamber unit main body and a plurality of rotating operating units provided in the lens chamber unit main body are formed.

4. The optometry apparatus controller according to claim 3, wherein:
the plurality of rotating operating units of the graphic image includes a spherical disc for modifying the spherical diopter power of the optical element of the optometry apparatus main body, an astigmatic axis conversion knob having a display formed in a smaller size than the spherical disc and for converting the astigmatic axis of the optical element of the optometry apparatus main body, and a cylindrical power conversion knob for converting the cylindrical power of the optical element of the optometry apparatus main body; and
based on a touch input with respect to the spherical disc, the astigmatic axis conversion knob, and the cylindrical power conversion knob on the touchscreen, a control signal for modifying the refractive power of the optical element is output to the optometry apparatus main body.

5. The optometry apparatus controller according to claim 2, wherein the operation screen, the controller further displays, as the operation screen, a graphic image including a movable unit for moving the lens chamber unit main body, and a pupillary distance adjusting knob provided in the movable unit.

6. The optometry apparatus controller according to claim 2, wherein the graphic image in which a display region for displaying optical characteristics of the optical element of the optometry apparatus main body disposed in front of the examinee's eye is formed.

7. The optometry apparatus controller according to claim 6, wherein:
the display region is a scale formed outside the rotating operating unit of the graphic image, with a reference mark formed on the rotating operating unit of the graphic image; and
the controller displays the rotating operating unit of the graphic image so as to be moved with respect to the scale in accordance with an operation with respect to the rotating operating unit of the graphic image.

8. The optometry apparatus controller according to claim 2, wherein, in accordance with a procedure of an optometry program including a subjective refractive power examination procedure set in advance for the examinee's eye, the rotating operating unit of the graphic image that is to be operated next is displayed with emphasis relative to the other rotating operating units.

9. The optometry apparatus controller according to claim 2, comprising an informing unit that informs of the switching of the optical element of the optometry apparatus main body.

10. The optometry apparatus controller according to claim 9, characterized in that the informing unit informs of the switching of the optical element of the optometry apparatus main body using a voice generator or a vibrator provided in the controller.

11. A non-transitory computer-readable storage medium having stored therein an optometry apparatus program for causing a computer with a touchscreen to function as an optometry apparatus controller for providing an instruction for switching an optical element of an optometry apparatus main body including the optical element disposed in front of an examinee's eye and a switch unit that electrically switches the optical element,
the program causing the computer to function as:
a touch input detection unit that detects a touch input from the touchscreen;
a display control unit that causes an operation screen for operating the optometry apparatus main body to be displayed on the touchscreen, the display control unit causing a graphic image of a manual refractor as viewed from the operator side to be displayed as the operation screen, the manual refractor including a lens chamber unit and a plurality of rotating operating units provided in the lens chamber unit, and being configured to mechanically switch the optical element disposed in front of the eye by a rotating operation with respect to the plurality of rotating operating units;
an output unit that outputs a control signal to the optometry apparatus main body based on the touch input with respect to the graphic image on the touchscreen; and
the optometry apparatus main body that switches a plurality of diopter powers of the optical element included in the optometry apparatus main body based on the touch input with respect to the graphic image on the touchscreen.

12. The optometry apparatus controller according to claim 1, wherein:
a first graphic image indicating a trial frame main body including a lens attaching portion enabling manual replacement of a trial frame lens, and a second graphic image indicating a trial lens are displayed as the operation screen; and
the control signal is output to the optometry apparatus main body based on a touch input with respect to at least one of the first graphic image or the second graphic image on the touchscreen.

13. The optometry apparatus controller according to claim 12, wherein:
a selection screen for selecting the optical element disposed in front of the examinee's eye is displayed on the operation screen; and
a third graphic image indicating the optical element selected by the touch input with respect to the selection screen is displayed on the first graphic image.

14. The optometry apparatus controller according to claim 12, wherein, based on a drag operation or a flick operation on the second graphic image toward the first graphic image, a control signal for modifying the optical element is output to the optometry apparatus main body.

15. The optometry apparatus controller according to claim 12, wherein:
the second graphic image in which a spherical trial lens for modifying the spherical diopter power of the optical element, and an astigmatism trial lens for modifying the cylindrical power of the optical element are formed; and
a control signal for modifying the refractive power of the optical element is output to the optometry apparatus main body based on the touch input with respect to the spherical trial lens or the astigmatism trial lens.

16. The optometry apparatus controller according to claim 13, wherein, based on a rotating operation with respect to the third graphic image formed on the first graphic image, a control signal for modifying an axial angle of the optical element is output to the optometry apparatus main body.

17. The optometry apparatus controller according to claim 13, wherein:
the first graphic image includes an axial angle scale; and
the controller rotates the display of the third graphic image with respect to the axial angle scale in accordance with an operation with respect to the third graphic image formed on the first graphic image.

18. The optometry apparatus controller according to claim 12, wherein the control signal is output to the optometry apparatus main body based on a drag operation or a flick operation with respect to at least one of the first graphic image and the second graphic image.

19. The optometry apparatus controller according to claim 12, wherein at least a pair of left and right round frame portions is displayed as the first graphic image.

20. The optometry apparatus controller according to claim 1, comprising an operating unit for selecting the trial lens disposed in front of the examinee's eye, wherein:
a target display set for switching the optical element and a graphic image indicating a trial lens are displayed as the operation screen; and
based on a moving operation on the graphic image toward the target display, a control signal for disposing an optical element corresponding to the trial lens selected by the operating unit in advance at the examinee's eye is output to the optometry apparatus main body.

21. A non-transitory computer-readable storage medium having stored therein an optometry apparatus program for causing a computer with a touchscreen to function as an optometry apparatus controller for providing an instruction for switching an optical element of an optometry apparatus main body including the optical element disposed in front of an examinee's eye and a switch unit that electrically switches the optical element,
the program causing the computer to function as:
a touch input detection unit that detects a touch input from the touchscreen;
a display control unit that causes an operation screen for operating the optometry apparatus main body to be displayed on the touchscreen, the display control unit displaying, as the operation screen, a first graphic image indicating a trial frame main body including a lens attaching portion enabling manual replacement of a trial frame lens, and a second graphic image indicating the trial lens;
an output unit that outputs a control signal to the optometry apparatus main body based on a touch input with respect to at least one of the first graphic image or the second graphic image on the touchscreen; and
the optometry apparatus main body that switches a plurality of diopter powers of the optical element included in the optometry apparatus main body based on the touch input with respect to the second graphic image on the touchscreen.

22. A non-transitory computer-readable storage medium having stored therein an optometry apparatus program for causing a computer with a touchscreen to function as an optometry apparatus controller for providing an instruction for switching an optical element of an optometry apparatus main body including the optical element disposed in front of an examinee's eye and a switch unit that electrically switches the optical element,
the program causing the computer to function as:
a touch input detection unit that detects a touch input from the touchscreen;
a display control unit that causes an operation screen for operating the optometry apparatus main body to be displayed on the touchscreen, the display control unit displaying, as the operation screen, a target display set for switching the optical element and a graphic image indicating a trial lens;
an output unit that outputs, to the optometry apparatus main body and based on a moving operation of the graphic image toward the target display, a control signal for disposing the optical element corresponding to the trial lens selected from a plurality of trial lenses in advance at the examinee's eye; and
the optometry apparatus main body that switches a plurality of diopter powers of the optical element included in the optometry apparatus main body based on the touch input with respect to the graphic image on the touchscreen.

23. An optometry system for examining an examinee's eye, the system comprising:
the optometry apparatus controller according to claim 1; and
an optometry apparatus main body including an optical element disposed in front of an examinee's eye and a switch unit that electrically switches the optical element.

24. The optometry apparatus controller according to claim 1, wherein the graphic image comprises a spherical disc for modifying a spherical diopter power of the optical element of the electric optometry apparatus main body.

* * * * *